United States Patent
Shih et al.

(10) Patent No.: US 11,679,102 B2
(45) Date of Patent: Jun. 20, 2023

(54) METHOD FOR INHIBITING VIRUS INFECTION AND REPLICATION

(71) Applicant: Chang Gung University, Taoyuan (TW)

(72) Inventors: Shin-Ru Shih, New Taipei (TW); Yu-An Kung, Taoyuan (TW); Huan-Jung Chiang, Taoyuan (TW); Chuan-Tien Hung, Taichung (TW); Yu-Nong Gong, Taoyuan (TW); Hsin-Ping Chiu, Taoyuan (TW); Chiung-Guei Huang, Taoyuan (TW); Peng-Nien Huang, Taoyuan (TW); Sheng-Yu Huang, Taoyuan (TW)

(73) Assignee: Chang Gung University, Taoyuan (TW)

( * ) Notice: Subject to any disclaimer, the term of this patent is extended or adjusted under 35 U.S.C. 154(b) by 46 days.

(21) Appl. No.: 17/333,117

(22) Filed: May 28, 2021

(65) Prior Publication Data
US 2021/0386702 A1    Dec. 16, 2021

Related U.S. Application Data

(60) Provisional application No. 63/037,889, filed on Jun. 11, 2020.

(51) Int. Cl.
| | |
|---|---|
| *A61P 31/16* | (2006.01) |
| *A61K 31/4436* | (2006.01) |
| *A61K 31/131* | (2006.01) |
| *A61K 31/245* | (2006.01) |
| *A61K 31/427* | (2006.01) |
| *A61K 31/4439* | (2006.01) |
| *A61K 31/499* | (2006.01) |
| *A61K 9/00* | (2006.01) |

(52) U.S. Cl.
CPC ........ *A61K 31/4436* (2013.01); *A61K 9/0053* (2013.01); *A61K 31/131* (2013.01); *A61K 31/245* (2013.01); *A61K 31/427* (2013.01); *A61K 31/4439* (2013.01); *A61K 31/499* (2013.01); *A61P 31/16* (2018.01)

(58) Field of Classification Search
CPC .... A61K 31/55; A61K 9/2027; A61K 9/2054; A61K 9/2866; A61K 31/4436; A61K 31/131; A61K 31/245; A61K 31/427; A61K 31/4439; A61K 31/499
See application file for complete search history.

(56) References Cited

U.S. PATENT DOCUMENTS

2010/0136122 A1*  6/2010  Okochi .............. A61K 31/4439
                                              514/342

OTHER PUBLICATIONS

Carboni et al. (Med Hypotheses; 140: 109776. Published online Apr. 22, 2020. doi: 10.1016/j.mehy.2020.109776.) (Year: 2020).*

* cited by examiner

*Primary Examiner* — Jeffrey S Lundgren
*Assistant Examiner* — Chris E Simmons
(74) *Attorney, Agent, or Firm* — Cesari & McKenna, LLP

(57) ABSTRACT

Disclosed herein is a method for inhibiting virus infection, including administering to a subject in need thereof an effective amount of a ferroptosis inhibitor or a pharmaceutically acceptable salt thereof. Also disclosed is a method for inhibiting viral replication, including contacting a virus with a ferroptosis inhibitor or a pharmaceutically acceptable salt thereof.

3 Claims, 15 Drawing Sheets

Specification includes a Sequence Listing.

SEQUENCE LISTING

<160> NUMBER OF SEQ ID NOS: 8

<210> SEQ ID NO 1
<211> LENGTH: 18
<212> TYPE: DNA

```
<213> ORGANISM: Artificial Sequence
<220> FEATURE:
<223> OTHER INFORMATION: Forward primer for 5' UTR of enterovirus

<400> SEQUENCE: 1
ccctgaatgc ggctaatc                                                  18

<210> SEQ ID NO 2
<211> LENGTH: 20
<212> TYPE: DNA
<213> ORGANISM: Artificial Sequence
<220> FEATURE:
<223> OTHER INFORMATION: Reverse primer for 5' UTR of enterovirus

<400> SEQUENCE: 2
attgtcacca taagcagcca                                                20

<210> SEQ ID NO 3
<211> LENGTH: 21
<212> TYPE: DNA
<213> ORGANISM: Artificial Sequence
<220> FEATURE:
<223> OTHER INFORMATION: Forward primer for actin

<400> SEQUENCE: 3
gctcgtcgtc gacaacggct c                                              21

<210> SEQ ID NO 4
<211> LENGTH: 26
<212> TYPE: DNA
<213> ORGANISM: Artificial Sequence
<220> FEATURE:
<223> OTHER INFORMATION: Reverse primer for actin

<400> SEQUENCE: 4
caaacatgat cctgggtcat cttctc                                         26

<210> SEQ ID NO 5
<211> LENGTH: 21
<212> TYPE: DNA
<213> ORGANISM: Artificial Sequence
<220> FEATURE:
<223> OTHER INFORMATION: Short hairpin RNA targeting human ACSL4 mRNA at
      nucleotide positions 485 to 505

<400> SEQUENCE: 5
ccagtgttga acttctggaa a                                              21

<210> SEQ ID NO 6
<211> LENGTH: 21
<212> TYPE: DNA
<213> ORGANISM: Artificial Sequence
<220> FEATURE:
<223> OTHER INFORMATION: Short hairpin RNA targeting human ACSL4 mRNA at
      nucleotide positions 439 to 459

<400> SEQUENCE: 6
gcagtagttc atgggctaaa t                                              21

<210> SEQ ID NO 7
<211> LENGTH: 23
<212> TYPE: DNA
<213> ORGANISM: Artificial Sequence
<220> FEATURE:
<223> OTHER INFORMATION: Scramble control short hairpin RNA

<400> SEQUENCE: 7
```

```
aatttgcgcc cgcttaccca gtt                                           23

<210> SEQ ID NO 8
<211> LENGTH: 20
<212> TYPE: DNA
<213> ORGANISM: Artificial Sequence
<220> FEATURE:
<223> OTHER INFORMATION: Single guide RNA targeting human ACSL4 mRNA at
      nucleotide positions 386 to 405

<400> SEQUENCE: 8
aggaaagttg tacttaaagc                                               20
```

METHOD FOR INHIBITING VIRUS INFECTION AND REPLICATION

CROSS-REFERENCE TO RELATED APPLICATION

This application claims priority of U.S. Provisional Application No. 63/037,889, filed on Jun. 11, 2020.

FIELD

The present disclosure relates to a method for inhibiting virus infection and replication using a ferroptosis inhibitor.

BACKGROUND

RNA viruses are typically classified based on their genome, (i.e., double-stranded, negative sense single-strand, or positive sense single-strand), gene number and organization. At present, RNA viruses are classified into 5 orders and 47 families, including many unassigned genera and species thereof. Among these 47 families, certain members of the Picornaviridae family, Orthomyxoviridae family, Flaviviridae family, and Coronaviridae family are actively researched since they infect and cause notable clinical symptoms in humans.

Enterovirus is a genus of positive sense single-strand RNA viruses belonging to the Picornaviridae family, and includes fifteen species, namely, Enterovirus A to L and Rhinovirus A to C. Till date, more than 200 serotypes of enteroviruses infecting humans have been identified based on antibody neutralization test, and additional antigenic variants have been defined within several of these serotypes. Enterovirus infection can result in a wide variety of clinical manifestations, including mild respiratory illness (i.e., common cold), hand-foot-and-mouth-disease (HFMD), herpangina, acute hemorrhagic conjunctivitis, acute flaccid paralysis, acute flaccid myelitis, encephalitis, pericarditis, myocarditis, meningitis, epidemic pleurodynia, neonatal sepsis-like disease, neurogenic pulmonary edema, and even death. The vast number of serotypes of enteroviruses makes it challenging to develop vaccines that can target multiple enteroviruses.

Influenza A virus (JAY) is the only species of the genus *Alphainfluenzavirus* that belongs to the Orthomyxoviridae family which has a negative sense single-strand segmented RNA genome, and is further classified into different subtypes based on the distinction of two large glycoproteins present on the surface of the virus, i.e., hemagglutinin and neuraminidase. Influenza A virus infection causes influenza, commonly known as "flu", which is a contagious acute respiratory disease, and seasonal influenza outbreaks occur every year, mainly during winter in Northern and Southern Hemispheres, occasionally giving rise to human influenza pandemics. In humans, symptoms of influenza usually include fever, chills, cough, sore throat, muscle pain, fatigue, and if severity of infection worsens, might result in health complications such as pneumonia, encephalitis, pericarditis, etc., which might be fatal. Although influenza vaccines are available and are generally safe, new versions of the vaccines need to be developed every year as influenza A virus undergoes rapid changes, e.g., genome mutations, while viral strains have emerged to show increasingly prevalent resistance to current influenza antivirals (e.g., neuraminidase inhibitors and M2 protein inhibitors).

Zika virus is a positive sense single-strand RNA virus classified under the genus Flavivirus which belongs to the Flaviviridae family. Infection with Zika virus causes Zika fever (also known as Zika virus disease) that is usually asymptomatic or is presented with mild symptoms including fever, red eyes, joint pain, headache, and a maculopapular rash. However, mother-to-child transmission during pregnancy can cause microcephaly, severe brain malformations and other congenital defects, and infections in adults have been linked to Guillain-Barré syndrome. Until now, no specific treatment and clinically-approved vaccines are available for treating and preventing Zika virus disease.

Coronaviruses are a group of positive-sense, single-strand RNA viruses belonging to the Coronaviridae family, which includes seven species/strains that infect humans, i.e., human coronavirus OC43 (HCoV-OC43), human coronavirus HKU1 (HCoV-HKU1), human coronavirus 229E (HCoV-229E), human coronavirus NL63 (HCoV-NL63), Middle East respiratory syndrome-related coronavirus (MERS-CoV), severe acute respiratory syndrome coronavirus (SARS-CoV), and severe acute respiratory syndrome coronavirus 2 (SARS-CoV-2). Notably, SARS-CoV-2 is identified as the viral strain causing the current outbreak of coronavirus disease 2019 (COVID-19), the rapid spread of which was declared as a global pandemic known as COVID-19 pandemic. Symptoms of COVID-19 may be relatively non-specific, including fever, cough, fatigue, phlegm production, loss of sense of smell, shortness of breath, muscle and joint pain, headache, and chills, among others. Further development of COVID-19 symptoms may lead to complications, including breathing difficulties, pneumonia, acute respiratory distress syndrome, sepsis, septic shock, multi-organ failure, and death. Even though several COVID-19 vaccines have demonstrated high efficacy in preventing symptomatic COVID-19 infections during Phase III clinical trials, all potential adverse effects from such vaccines may not be known until use in general population (i.e., until post-marketing surveillance trials are conducted).

Therefore, there is a need to seek broad-spectrum antiviral drugs that can effectively inhibit the infection and replication of the aforesaid viruses.

SUMMARY

Therefore, an object of the present disclosure is to provide a method for inhibiting virus infection which can alleviate at least one of the drawbacks of the prior art.

According to the present disclosure, the method for inhibiting virus infection includes administering to a subject in need thereof an effective amount of a ferroptosis inhibitor or a pharmaceutically acceptable salt thereof.

Another object of the present disclosure is to provide a method for inhibiting viral replication which can alleviate at least one of the drawbacks of the prior art.

According to the present disclosure, the method for inhibiting viral replication includes contacting a virus with a ferroptosis inhibitor or a pharmaceutically acceptable salt thereof.

BRIEF DESCRIPTION OF THE DRAWINGS

Other features and advantages of the present disclosure will become apparent in the following detailed description of the embodiments with reference to the accompanying drawings, of which.

Figure 2:
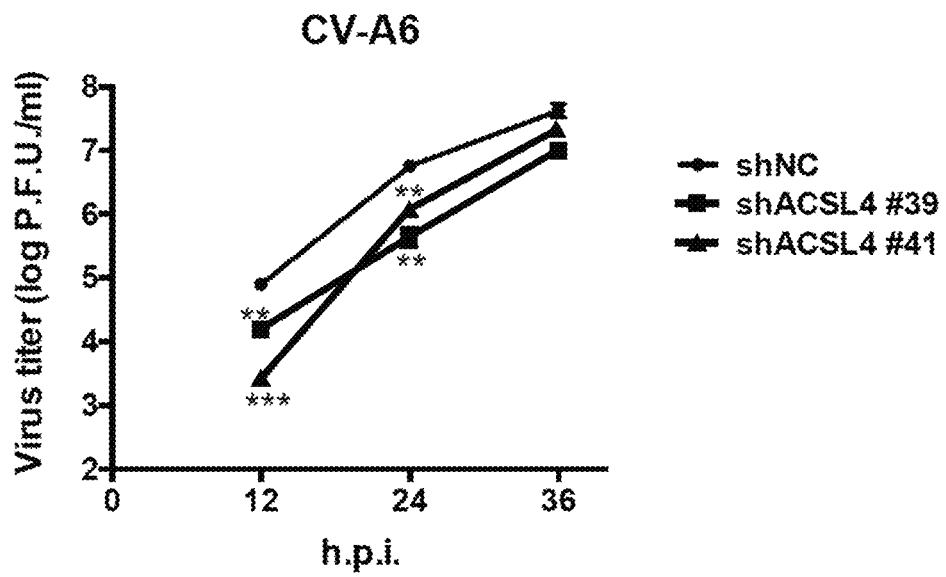
Figure 2:
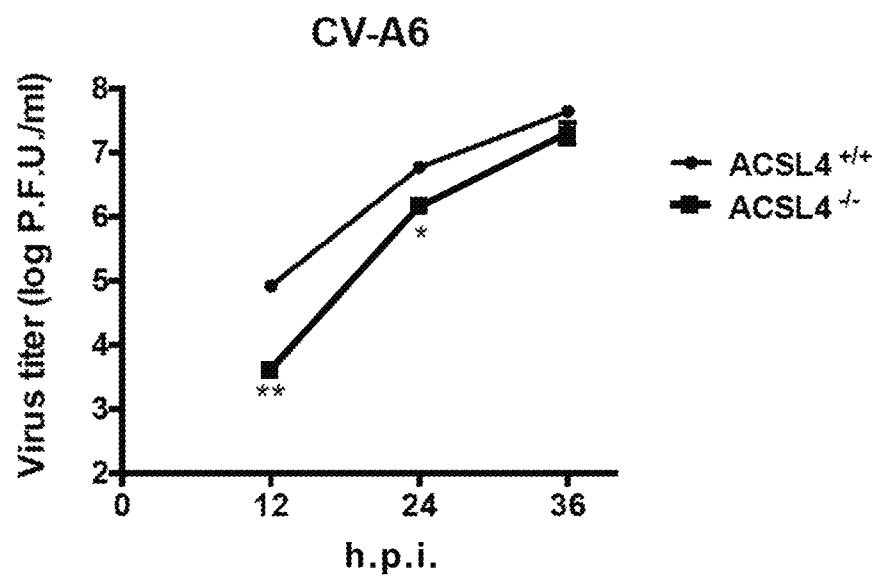
Figure 3:
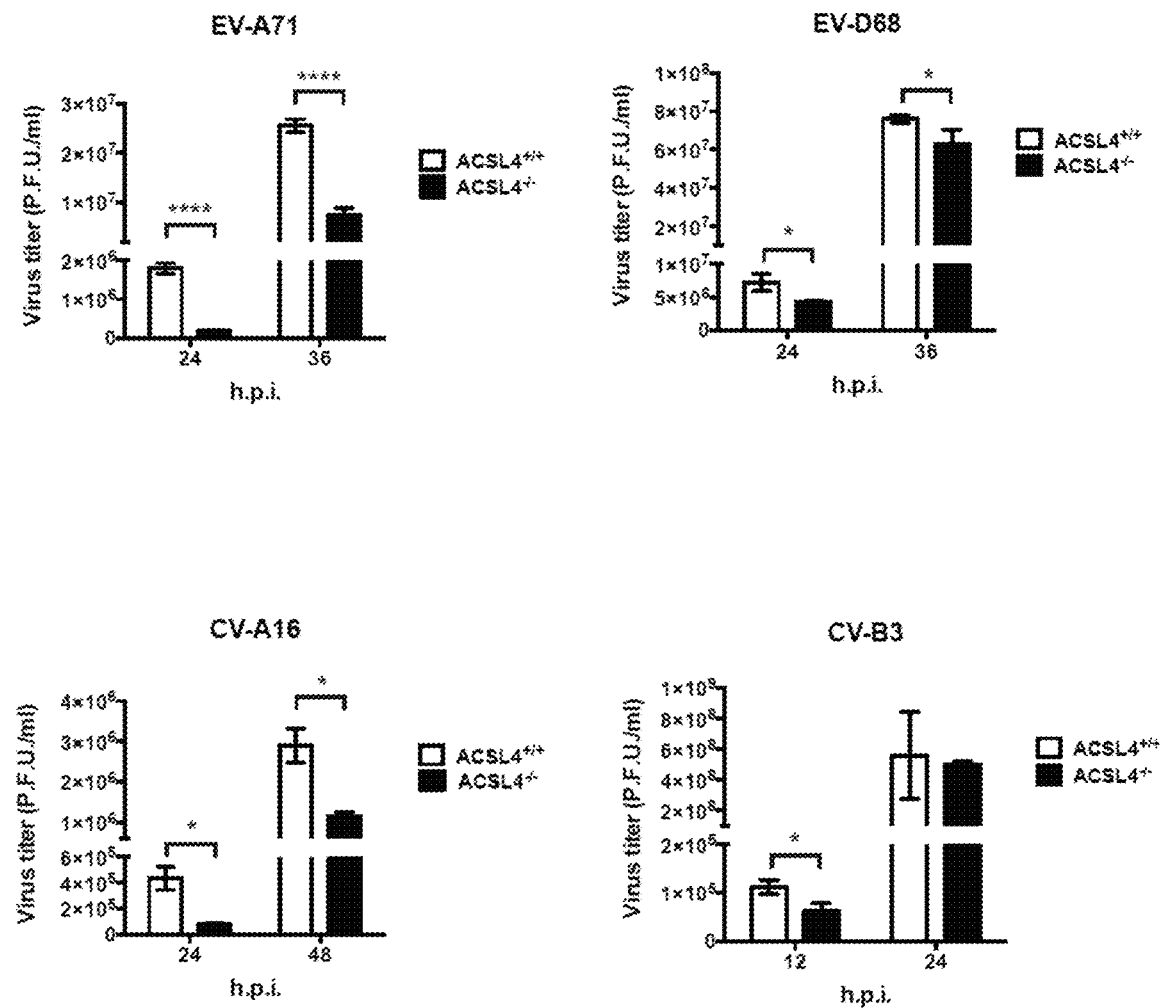
Figure 4:
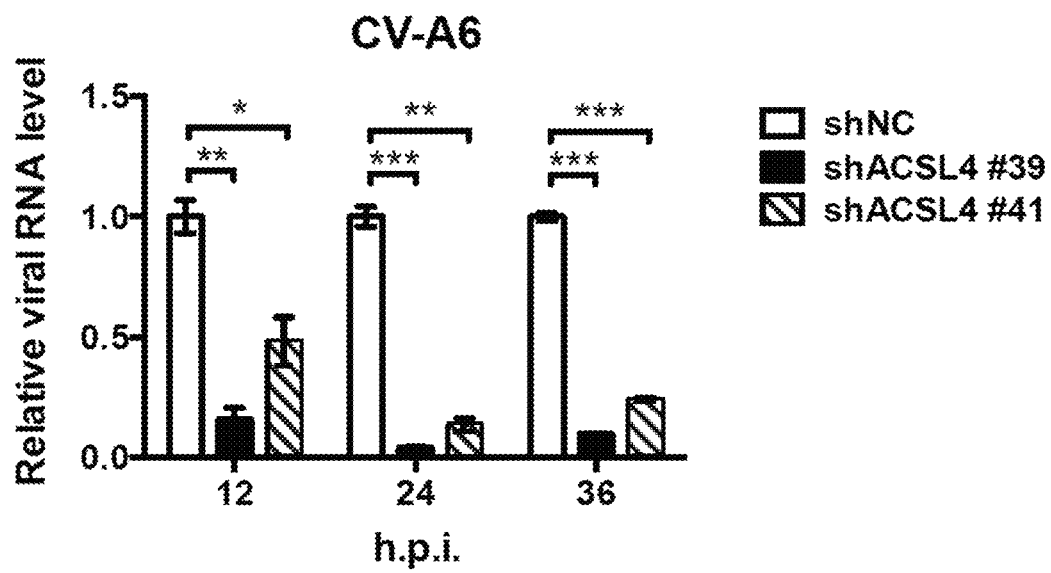
Figure 4:
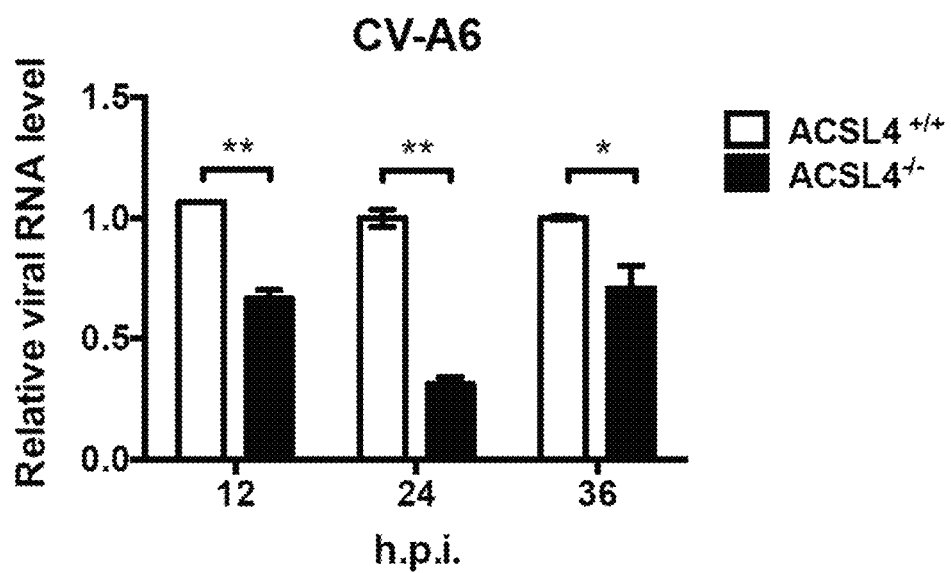
Figure 5:
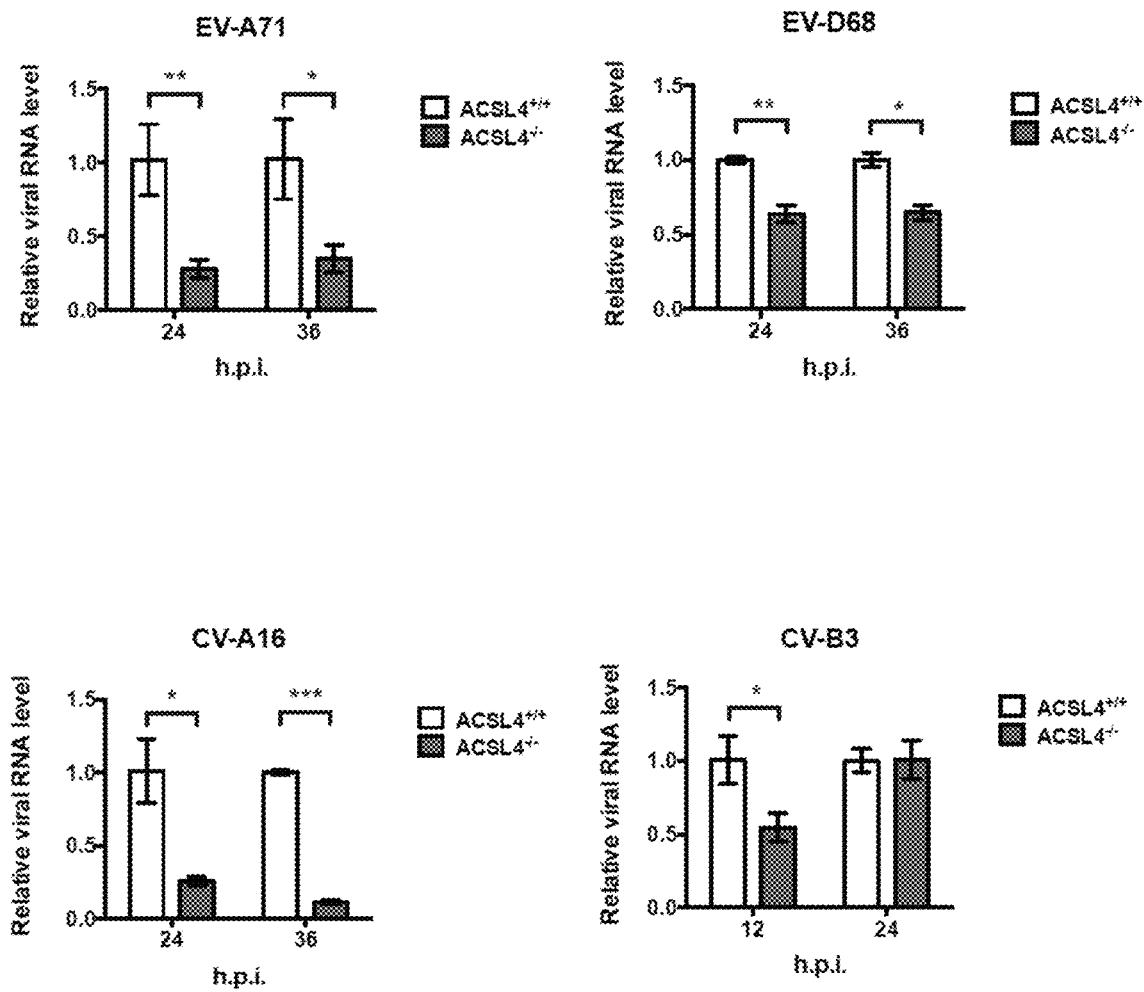
Figure 6:
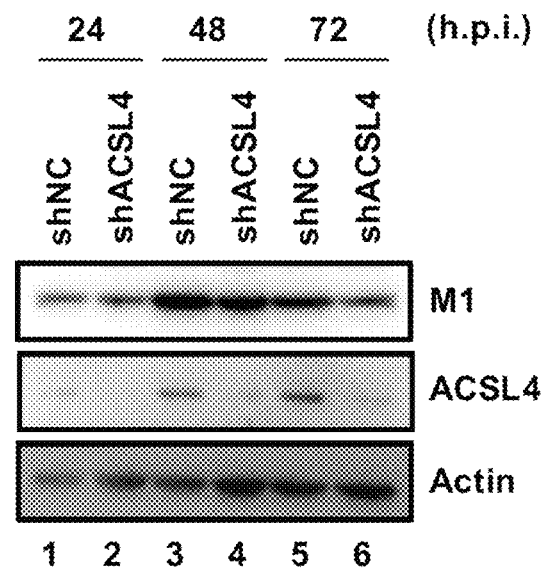
Figure 6:
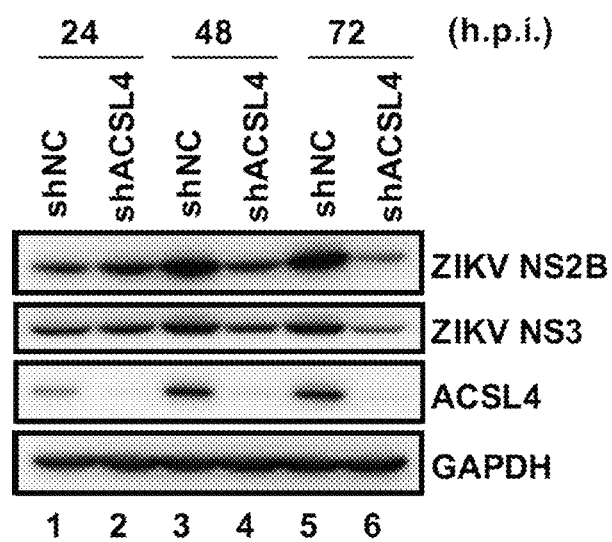
Figure 7:
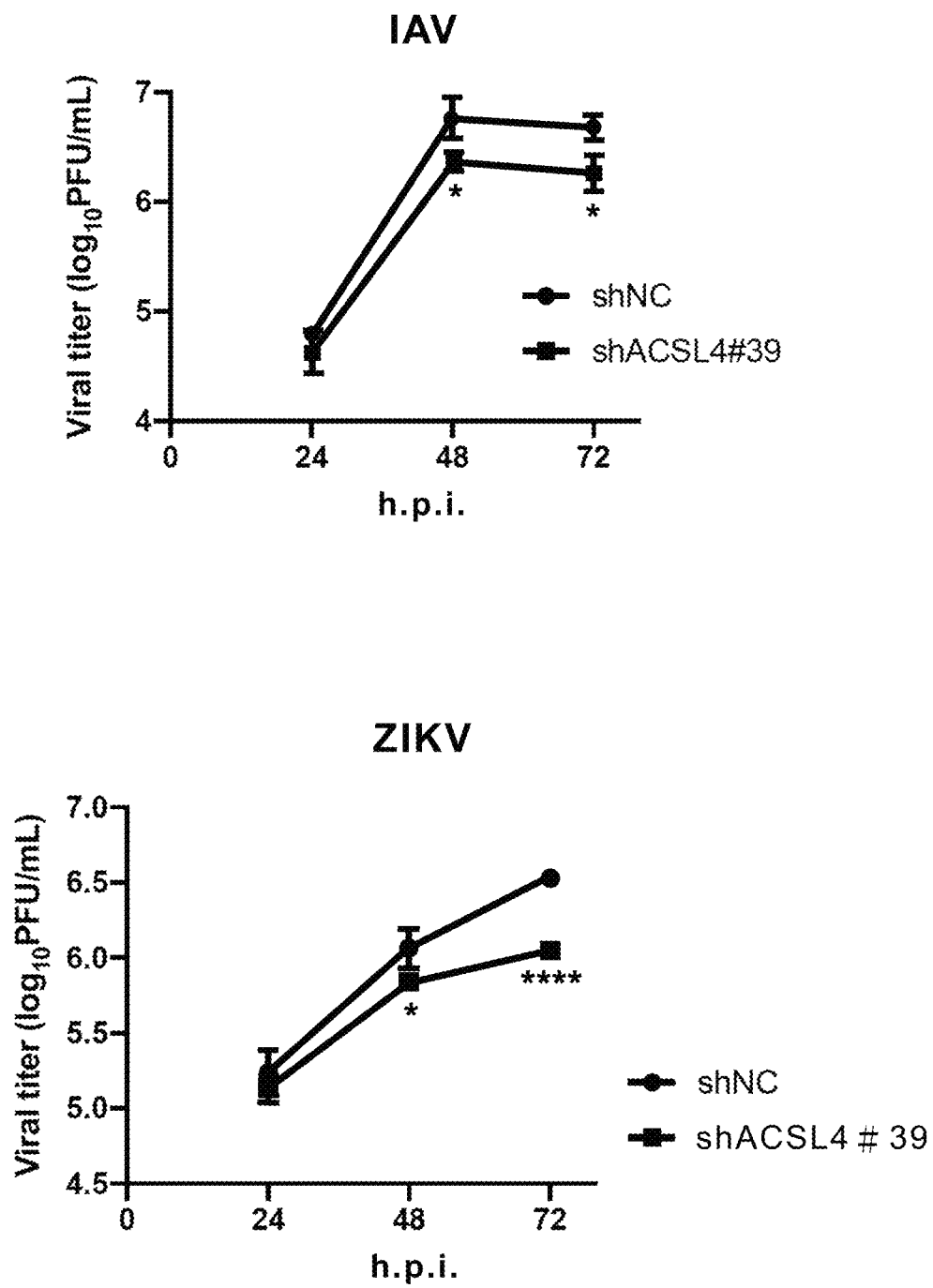
Figure 8:
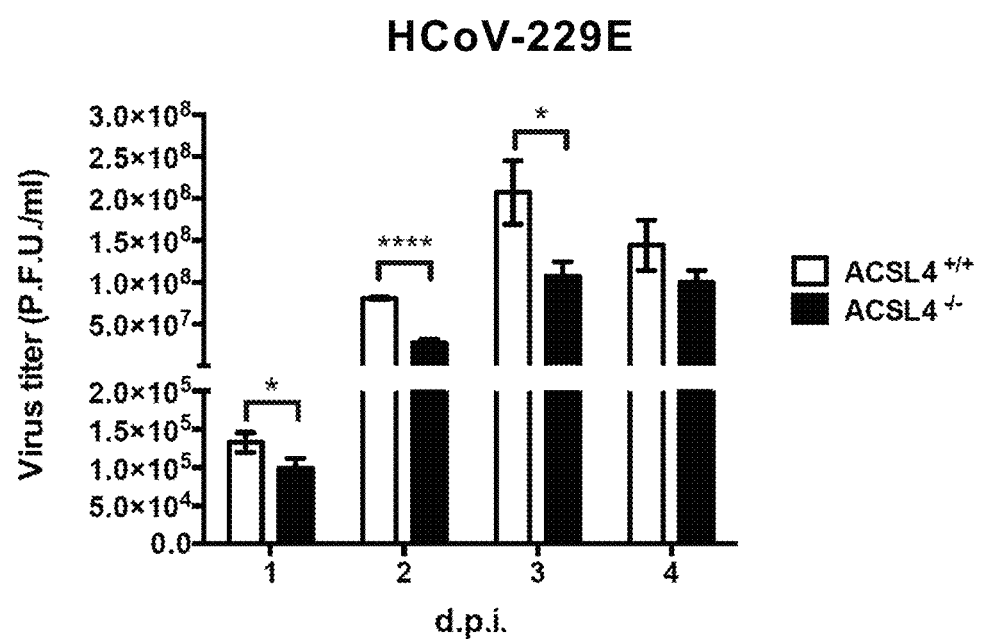
Figure 9:
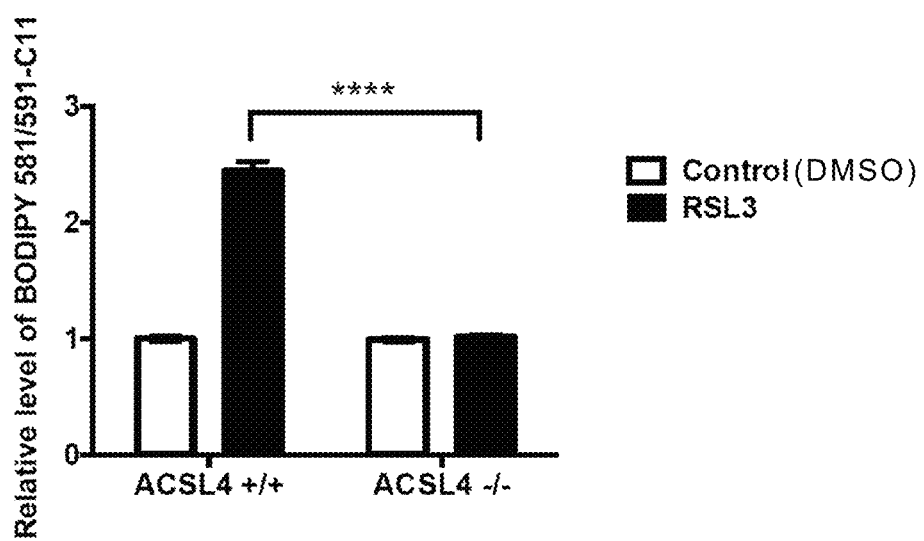
Figure 9:
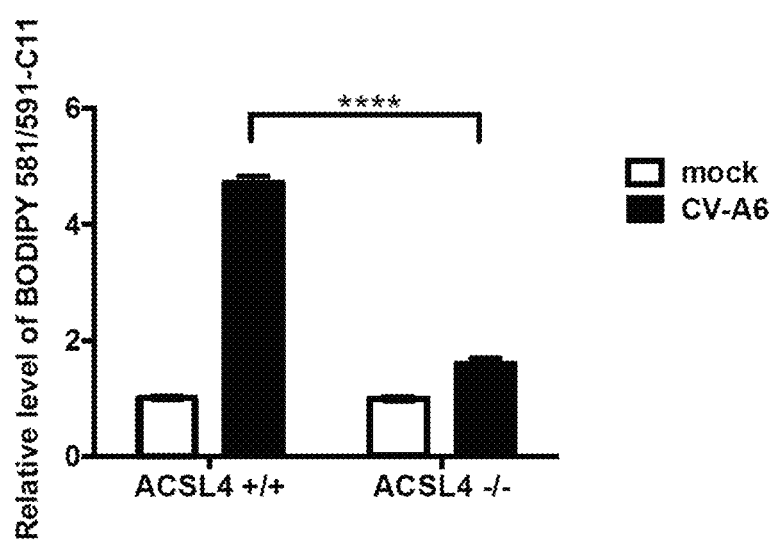
Figure 10:
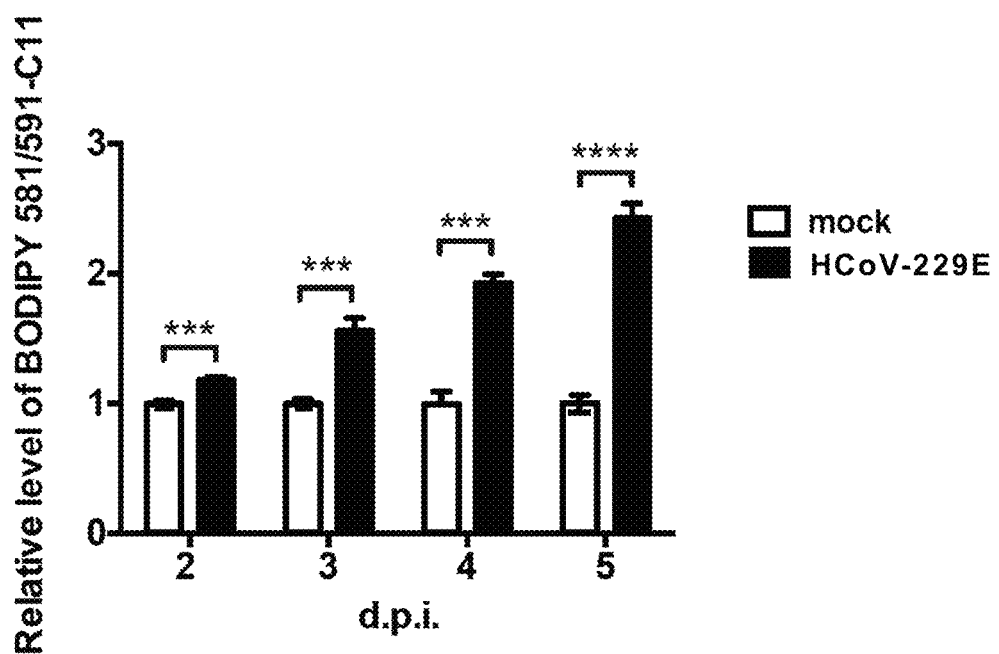
Figure 11:
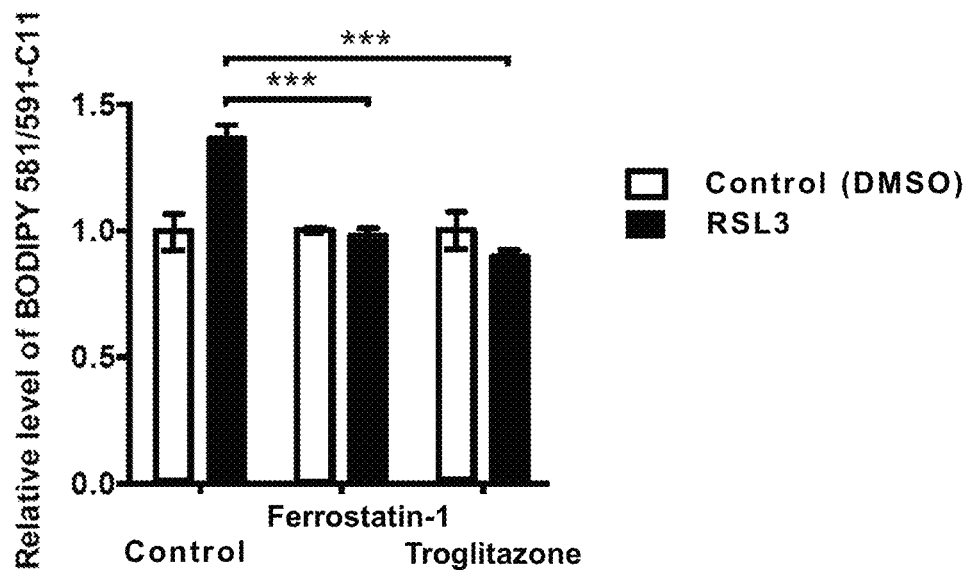
Figure 11:
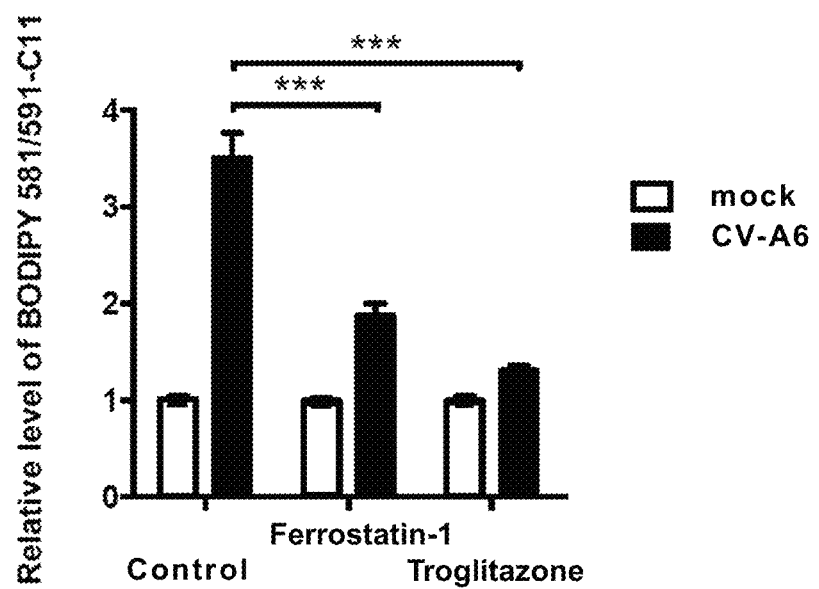
Figure 12:
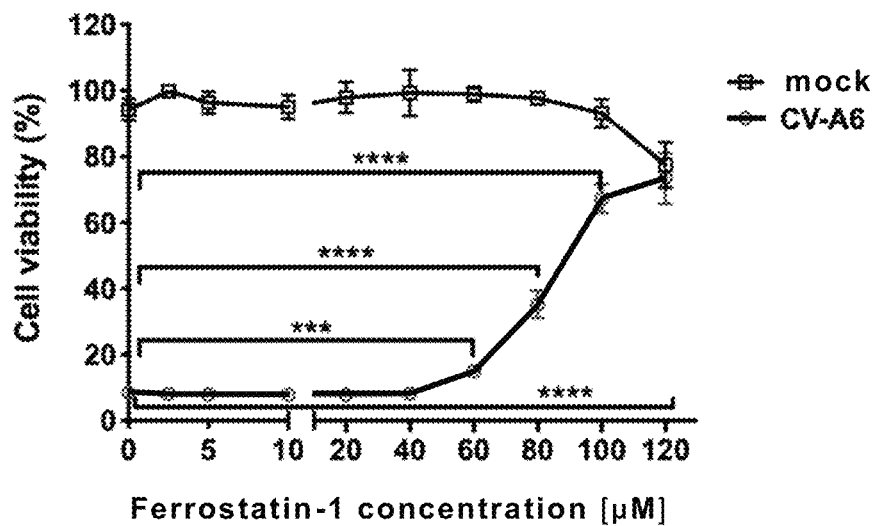
Figure 12:
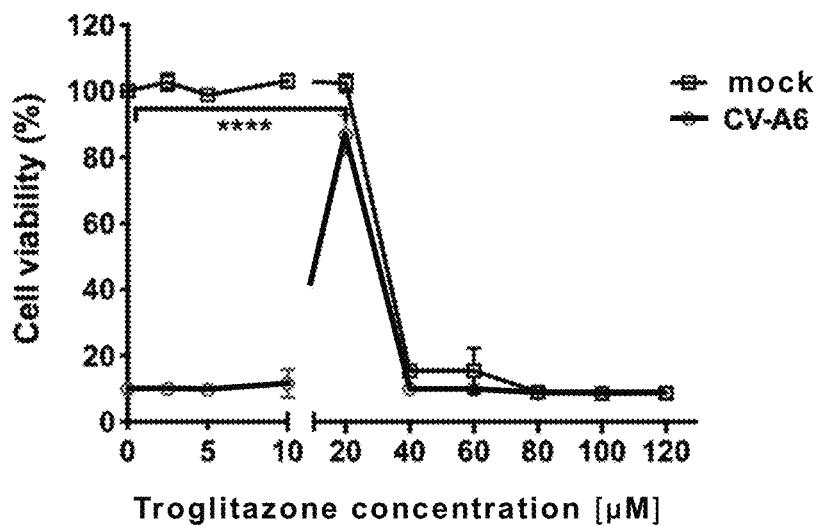
Figure 13:
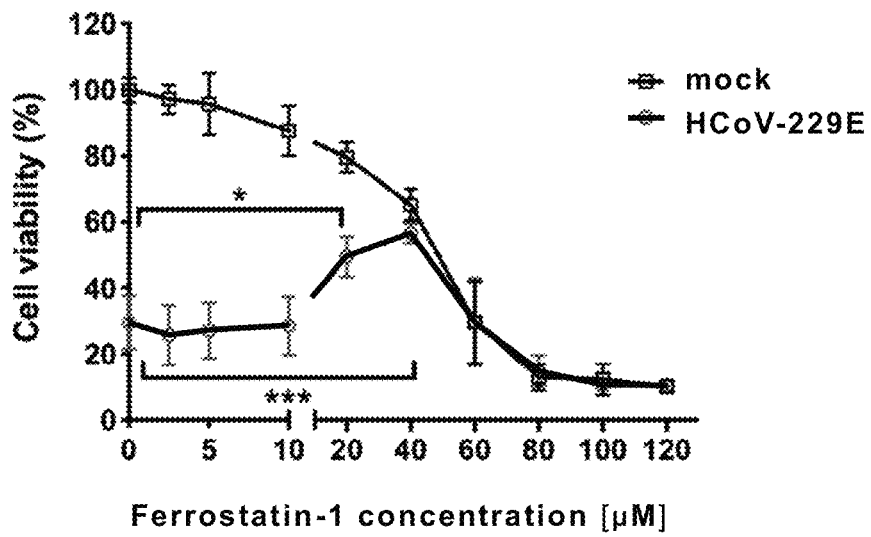
Figure 13:
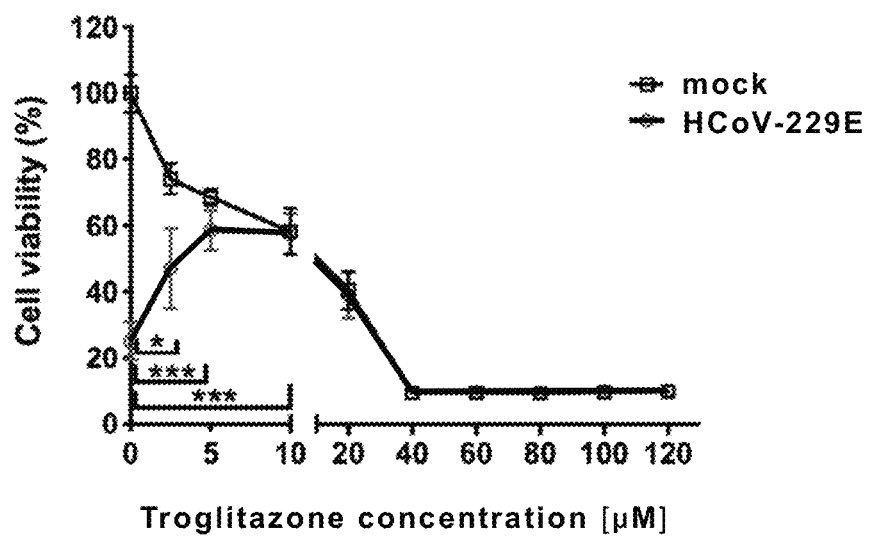
Figure 14:
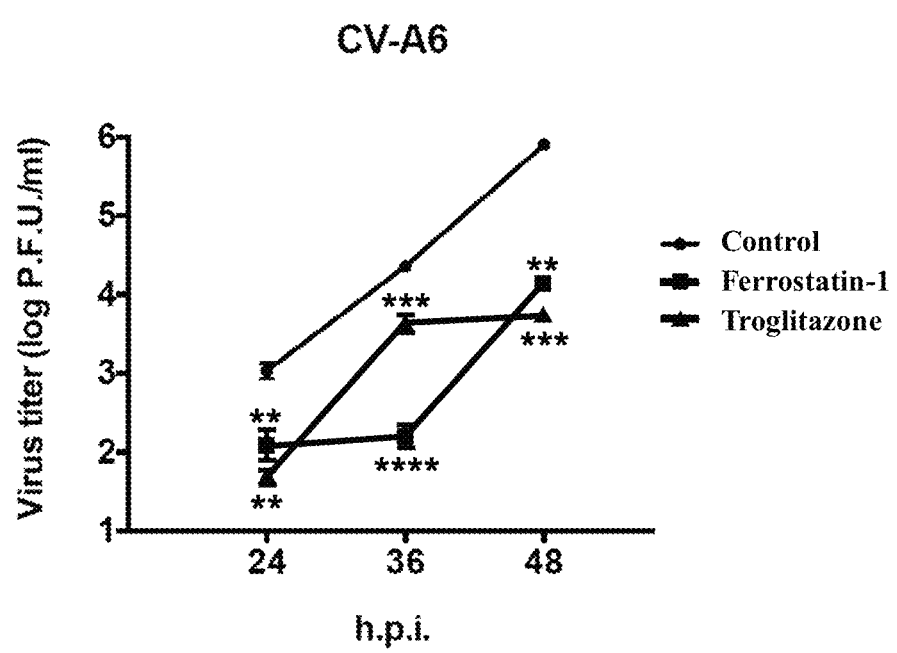
Figure 15:
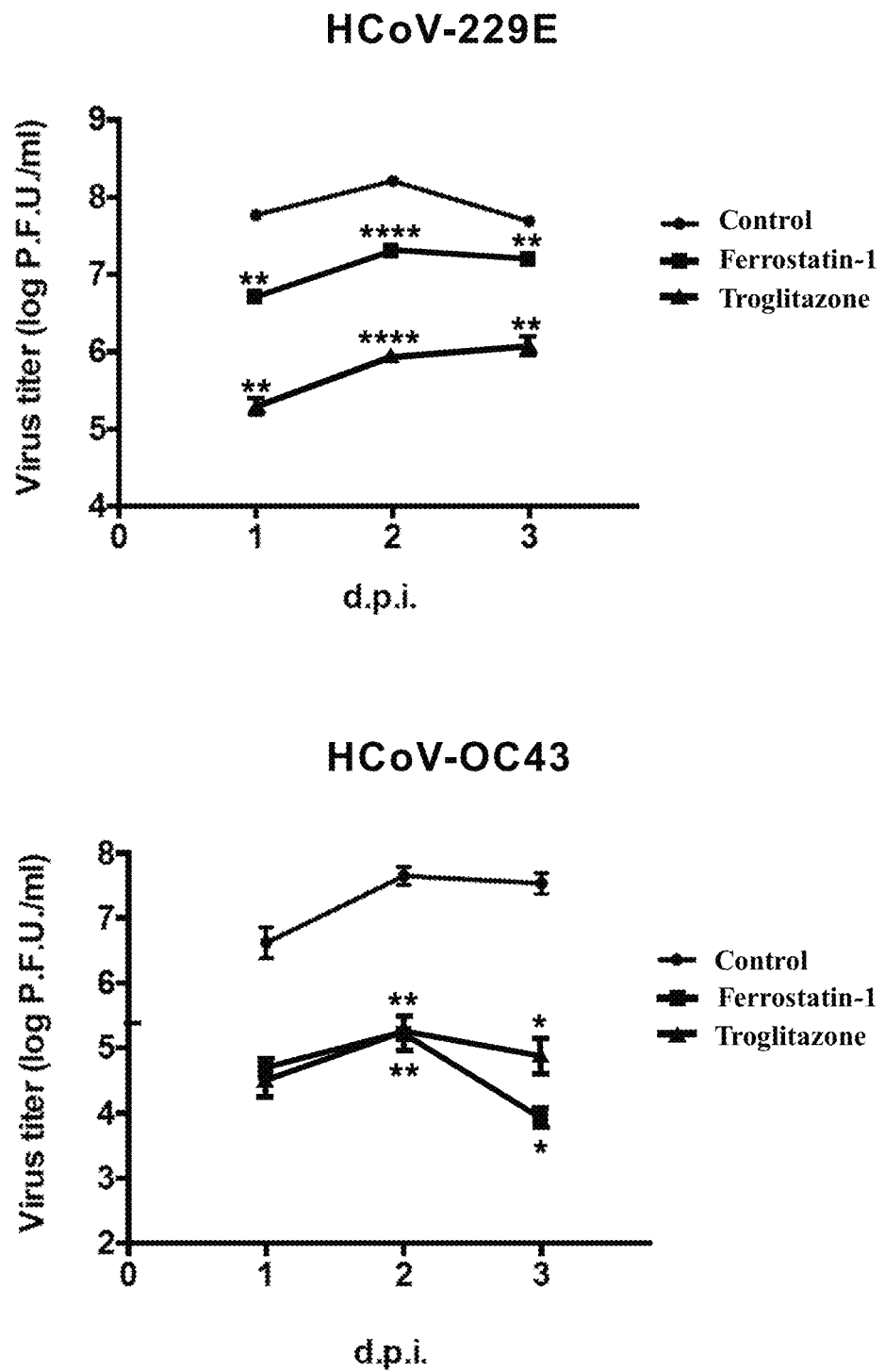

FIG. 2 shows virus titers of CV-A6 in infected shACSL4#39 and shACSL4#41 knockdown cells and shNC control cells (upper panel) and in infected sgACSL4$^{-/-}$ knockout cells and sgACSL4$^{+/+}$ control cells (lower panel) at 12, 24, and 36 hours post-infection (h.p.i.), in which the symbols "*", "" and "*" respectively represent $p<0.05$, $p<0.01$ and $p<0.005$;

FIG. 3 shows virus titers of different enteroviruses (i.e., EV-A71, EV-D68, CV-A16 and CV-B3) in infected sgACSL4$^{-/-}$ knockout cells and sgACSL4$^{+/+}$ control cells at given h.p.i., in which the symbols "*" and "****" respectively represent $p<0.05$ and $p<0.001$;

FIG. 4 shows viral RNA expression level of CV-A6 in infected shACSL4#39 and shACSL4#41 knockdown cells and shNC control cells (upper panel) and in infected sgACSL4$^{-/-}$ knockout cells and sgACSL4$^{+/+}$ control cells (lower panel) at 12, 24, and 36 hours h.p.i., in which the symbols "*", "" and "*" respectively represent $p<0.05$, $p<0.01$ and $p<0.005$;

FIG. 5 viral RNA expression level of different enteroviruses (i.e., EV-A71, EV-D68, CV-A16 and CV-B3) in infected sgACSL4$^{-/-}$ knockout cells and sgACSL4$^{+/+}$ control cells at given h.p.i., in which the symbols "*", "" and "*" respectively represent $p<0.05$, $p<0.01$ and $p<0.005$;

FIG. 6 shows viral protein expression of IAV M1 in IAV-infected shACSL4#39 knockdown cells and shNC control cells at 24, 48 and 72 h.p.i., in which actin served as a loading control (upper panel), and viral protein expression of ZIKV NS2B and ZIKV NS3 in ZIKV-infected shACSL4#39 knockdown cells and shNC control cells at 24, 48 and 72 h.p.i., in which GAPDH served as a loading control (lower panel);

FIG. 7 shows virus titers of IAV and ZIKV in infected shACSL4#39 knockdown cells and shNC control cells at 24, 48 and 72 h.p.i., in which the symbols "*" and "****" respectively represent $p<0.05$ and $p<0.001$;

FIG. 8 shows virus titers of HCoV-229E in infected sgACSL4$^{-/-}$ knockout cells and sgACSL4$^{+/+}$ control cells at 1, 2, 3 and 4 days post-infection (d.p.i.), in which the symbols "*" and "****" respectively represent $p<0.05$ and $p<0.001$;

FIG. 9 shows lipid peroxidation levels of RSL3-treated and DMSO-treated sgACSL4$^{-/-}$ knockout cells and sgACSL4$^{+/+}$ control cells at 36 hours post treatment (h.p.t.) (upper panel), and lipid peroxidation levels of CV-A6-infected and mock-infected sgACSL4$^{-/-}$ knockout cells and sgACSL4$^{+/+}$ control cells at 36 h.p.i. (lower panel), in which the symbol "****" represents $p<0.001$;

FIG. 10 shows lipid peroxidation levels of HCoV-229E-infected and mock-infected LLC-MK2 cells at 2, 3, 4, and 5 d.p.i., in which the symbols "*" and "**" respectively represent $p<0.005$, and $p<0.001$;

FIG. 11 shows lipid peroxidation levels of RSL3-treated and DMSO-treated RD cells pretreated with a respective one of ferrostatin-1 and troglitazone at 36 h.p.t. (upper panel), and lipid peroxidation levels of CV-A6-infected and mock-infected RD cells pretreated with a respective one of ferrostatin-1 and troglitazone at 36 h.p.i. (lower panel), in which the symbol "***" represents $p<0.005$;

FIG. 12 shows cell viability of mock-infected and CV-A6-infected RD cells pretreated with different concentrations of ferrostatin-1 (upper panel) and with different concentrations of troglitazone (lower panel) at 36 h.p.i., in which the symbols "*" and "**" respectively represent $p<0.005$ and $p<0.001$;

FIG. 13 shows cell viability of mock-infected and HCoV-229E-infected LLC-MK2 cells pretreated with different concentrations of ferrostatin-1 (upper panel) and with different concentrations of troglitazone (lower panel) at 7 d.p.i., in which the symbols "*" and "***" respectively represent $p<0.05$ and $p<0.005$;

FIG. 14 shows virus titers of CV-A6 in mock-infected and CV-A6-infected RD cells pretreated with a respective one of 100 μM ferrostatin-1 and 20 μM troglitazone at 24, 36, and 48 h.p.i., in which the symbols "" and "*" respectively represent $p<0.01$ and $p<0.005$; and FIG. 15 shows virus titers of HCoV-229E in mock-infected and HCoV-229E-infected LLC-MK2 cells pretreated with a respective one of 40 μM ferrostatin-1 and 10 μM troglitazone (upper panel) and virus titers of HCoV-OC43 in mock-infected and HCoV-OC43-infected Vero E6 cells pretreated with a respective one of 40 μM ferrostatin-1 and 10 μM troglitazone (lower panel) at 1, 2, and 3 d.p.i., in which the symbols "*", "" and "**" respectively represent $p<0.05$, $p<0.01$, and $p<0.001$.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In the development of drugs that can be used to treat virus infection, the applicants unexpectedly found that virus infection can induce ferroptosis via Acyl-CoA synthetase long chain family member 4 (ASCL4), and that various ferroptosis inhibitors can significantly reduce the viral titer and inhibit viral replication in the infected host cells, e.g., by targeting ASCL4, and hence are expected to be effective against virus infection.

Therefore, the present disclosure is directed to use of a ferroptosis inhibitor or a pharmaceutically acceptable salt thereof in the manufacture of a medicament for inhibiting virus infection and/or replication.

The present disclosure also provides a method for inhibiting virus infection, including administering to a subject in need thereof an effective amount of the ferroptosis inhibitor or the pharmaceutically acceptable salt thereof.

Moreover, the present disclosure provides a method for inhibiting viral replication, including contacting a virus with the ferroptosis inhibitor or the pharmaceutically acceptable salt thereof.

Examples of the ferroptosis inhibitor may include, but are not limited to, ferrostatin-1, troglitazone, rosiglitazone, pioglitazone, triacsin C, liproxstatin-1 and combinations thereof.

The ferroptosis inhibitor or the pharmaceutically acceptable salt thereof may inhibit ASCL4.

As used herein, the term "administration" or "administering" means introducing, providing or delivering a predetermined active ingredient (e.g., the ferroptosis inhibitor or the pharmaceutically acceptable salt thereof) to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

As used herein, the term "pharmaceutically acceptable salt" refers to any salt, which, upon administration to the subject is capable of providing (directly or indirectly) a compound as described herein (e.g., ferrostatin-1 or troglitazone) without undue toxicity, irritation, allergic response and the like. In particular, "pharmaceutically acceptable salt" may encompass those approved by a regulatory agency of the federal or a state government or listed in the U.S. Pharmacopeia or other generally recognized pharmacopeia for use in animals, and more particularly in humans. The preparation of salts can be carried out by methods known in the art.

For instance, the pharmaceutically acceptable salts of the ferrostatin inhibitor may be acid addition salts, base addition salts or metallic salts, and they can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture thereof. Examples of the acid addition salts may include mineral acid addition salts such as, for example, hydrochloride, hydrobromide, hydroiodide, sulfate, nitrate, and phosphate; and organic acid addition salts such as, for example, acetate, maleate, fumarate, citrate, oxalate, succinate, tartrate, malate, mandelate, methanesulphonate, p-toluenesulphonate, 2-naphtalenesulphonate, and 1,2-ethanedisulphonate. Examples of the alkali addition salts may include inorganic salts such as, for example, ammonium; and organic alkali salts such as, for example, ethylenediamine, ethanolamine, N,N-dialkylenethanolamine, triethanolamine, choline, glucamine, and basic aminoacids salts. Examples of the metallic salts may include, for example, sodium, potassium, calcium, magnesium, aluminium, and lithium salts.

According to this disclosure, the virus infection is caused by a single-strand RNA virus selected from the group consisting of a member of Picornaviridae family, a member of Orthomyxoviridae family, a member of Flaviviridae family, a member of Coronaviridae family, and combinations thereof.

In certain embodiments, the single-strand RNA virus is selected from the group consisting of an enterovirus, an influenza virus, a flavivirus, a coronovirus, and combinations thereof.

Examples of the enterovirus may include, but are not limited to, Enterovirus A such as Coxsackie virus A6 (CV-A6), Coxsackie virus A16 (CV-A16) and Enterovirus A71 (EV-A71); Enterovirus B such as Coxsackie virus B serotypes (e.g., CV-B3), echoviruses and enterovirus serotypes; Enterovirus C such as poliovirus 1, poliovirus 2 and poliovirus 3; Enterovirus D such as Enterovirus D68 (EV-D68); and combinations thereof.

In an exemplary embodiment, the enterovirus is CV-A6. In another exemplary embodiment, the enterovirus is CV-A16. In yet another exemplary embodiment, the enterovirus is EV-A71. In still yet another exemplary embodiment, the enterovirus is CV-B3. In still yet another exemplary embodiment, the enterovirus is EV-D68.

Examples of the influenza virus may include, but are not limited to, influenza A virus (IAV) such as H1N1, influenza B virus, influenza C virus, influenza D virus, and combinations thereof. In an exemplary embodiment, the influenza virus is IAV.

Examples of the flavivirus may include, but are not limited to, Dengue virus, Zika virus, yellow fever virus, tick-borne encephalitis virus, West Nile virus, and combinations thereof. In an exemplary embodiment, the flavivirus is Zika virus.

Examples of the coronavirus may include, but are not limited to, a member of Alphacoronavirus genus such as human coronavirus 229E (HCoV-229E); a member of Betacorovirus genus such as human coronavirus OC43 (HCoV-OC43), severe acute respiratory syndrome coronavirus (SARS-CoV), and severe acute respiratory syndrome coronavirus 2 (SARS-CoV-2); a member of Gammacoronavirus genus such as Brangacovirus and Cegacovirus; a member of Deltacoronavirus genus such as Andecovirus, Buldecovirus and Herdecovirus; and combinations thereof.

In an exemplary embodiment, the coronavirus is HCoV-229E. In another exemplary embodiment, the coronavirus is HCoV-OC43.

According to this disclosure, the ferroptosis inhibitor or the pharmaceutically acceptable salt thereof may be prepared into a pharmaceutical composition in a dosage form suitable for, e.g., parenteral or oral administration, using technology well known to those skilled in the art. Examples of the dosage form may include, but are not limited to, sterile powder, tablets, troches, lozenges, capsules, dispersible powder, granule, solutions, suspensions, emulsions, syrup, elixirs, slurry, and the like.

Examples of the parenteral administration may include, but are not limited to, intraperitoneal injection, intrapleural injection, intramuscular injection, intravenous injection, intraarterial injection, intraarticular injection, intrasynovial injection, intrathecal injection, intracranial injection and sublingual administration.

According to this disclosure, the pharmaceutical composition may further include a pharmaceutically acceptable carrier that is widely employed in the art of drug-manufacturing. Examples of the pharmaceutically acceptable carrier may include, but are not limited to, solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the pharmaceutically acceptable carrier are within the expertise of those skilled in the art.

The dosage and the frequency of administration of the ferroptosis inhibitor or the pharmaceutically acceptable salt thereof may vary depending on the following factors: the severity of the illness/viral infection to be treated and the weight, age, physical condition and response of the subject to be treated. The daily dosage of the pharmaceutical composition may be administered in a single dose or in several doses.

The present disclosure will be further described by way of the following examples. However, it should be understood that the following examples are intended solely for the purpose of illustration and should not be construed as limiting the present disclosure in practice.

EXAMPLES

General Experimental Materials:
1. Ferrostatin-1 and troglitazone were purchased from Sigma-Aldrich.
2. Primers used in the following examples were synthesized by Tri-I Biotech Inc., Taiwan.
3. Cell Cultures Human muscle rhabdomyosarcoma (RD) cells (ATCC CCL-136), human embryonic kidney (293T) cells (ATCC CRL-3216), human lung adenocarcinoma epithelial (A549) cells (ATCC CCL-185), African green monkey kidney (Vero) cells (ATCC CCL-81), Madin-Darby canine kidney (MDCK) cells (ATCC CCL-34), Rhesus monkey kidney epithelial (LLC-MK2) cells (ATCC CCL-7) and African green monkey kidney (Vero E6) cells (ATCC CRL-1586) used in the following experiments were purchased from ATCC (American Type Culture Collection, Manassas, Va., USA). Human hepatoma cell lines (Huh-7) cells (Ser. No. 01/042,712) were purchased from Sigma-Aldrich. Each of RD cells, 293T cells, A549 cells, MDCK cells, Vero cells, and Huh-7 cells were incubated in a Petri dish containing Dulbecco's modified Eagle's medium (DMEM; Gibco, Grand Island, N.Y.) supplemented with 10% fetal bovine serum (FBS; Gibco), followed by cultivation in an incubator with culture conditions set at 37° C. and 5% $CO_2$.

Each of LLC-MK2 cells and Vero E6 cells were incubated in a Petri dish containing minimum essential medium (MEM; Gibco, Grand Island, N.Y.) supplemented with 10% fetal bovine serum (FBS; Gibco), followed by cultivation in an incubator with culture conditions set at 37° C. and 5% $CO_2$ for LLC-MK2 cells or 33° C. and 5% $CO_2$ for Vero-E6 cells. Medium change was performed every 3 days. Cell passage was performed when the cultured cells reached 80% to 90% of confluence.

4. Virus Strains
a) Enterovirus: Coxsackie virus A6 (CV-A6), Coxsackie virus A16 (CV-A16), Coxsackie virus B3 (CV-B3), Enterovirus A71 (EV-A71) strain Tainan/4643/98, and Enterovirus D68 (EV-D68) strain TW-02795-2014 were obtained from Chang-Gung Memorial Hospital, Linkou, Taiwan.
b) Influenza virus: Influenza A virus (IAV) strain A/WSN/1933 was generated using a reverse genetic system, and was kindly provided by Dr. Ervin Fodor, University of Oxford, UK.
c) Flavivirus: Zika virus (ZIKV) strain PRVABC59 was obtained from the Centers for Disease Control, Taiwan.
d) Coronavirus: Human coronavirus 229E (HCoV-229E) (ATCC VR-740) and human coronavirus OC43 (HCoV-OC43) (ATCC VR-1558) were purchased from ATCC (American Type Culture Collection, Manassas, Va., USA).

General Experimental Procedures:
1. Virus Infection

When the cultured cells reached 80% to 90% of confluence, infection at a given multiplicity of infection (m.o.i.) by CV-A6, CV-A16, CV-B3, EV-A71, EV-D68, IAV and ZIKV, was performed in serum-free DMEM, while that by HCoV-229E and HCoV-OC43 was performed in serum-free MEM. The viruses were allowed to adsorb at 37° C. (CV-A6, CV-A16, CV-B3, EV-A71, EV-D68, IAV, ZIKV and HCoV-229E) or 33° C. (HCoV-OC43) for 1 hour, after which the infected cells were washed with phosphate-buffered saline (PBS) and incubated at 37° C. or 33° C. in DMEM or MEM containing 2% FBS.

2. Western Blot Analysis

Protein samples were resolved in sodium dodecyl sulfate-polyacrylamide (SDS-PAGE) gels, and the separated proteins were subsequently transferred to polyvinylidene difluoride (PVDF) membranes (GE Healthcare). The blotted PVDF membranes thus obtained were blocked with tris-buffered saline (TBS) and 0.1% (vol/vol) polysorbate 20 (also known as Tween 20) containing 5% non-fat dry milk, followed by washing with TBST 3 times, each time for 15 minutes, and then probing with the indicated primary antibodies overnight. The probed membranes were washed with a TBST buffer (a mixture of TBS and polysorbate 20) 3 times, each time for 15 minutes, and were then incubated with secondary antibodies, such as a horseradish peroxidase (HRP)-conjugated anti-mouse antibody or an HRP-conjugated anti-rabbit antibody for 60 minutes at room temperature. HRP was detected using a Western Lightning™ Chemiluminescence Kit (PerkinElmer Life Sciences, Boston, Mass.).

3. Viral Plaque Assay

Each type of the tested viruses (CV-A6, CV-A16, CV-B3, EV-A71, EV-D68, IAV and ZIKV) was subjected to a ten-fold dilution using serum-free DMEM, and HCoV-229E and HCoV-OC43 were subjected to a ten-fold dilution using serum-free MEM, so as to obtain a respective diluted viral solution having a dilution factor of 10.

RD cells, MDCK cells, Vero cells, and Huh-7 cells were seeded at a concentration of $5\times10^5$ cells per well into respective wells of 6-well plates containing serum-free DMEM, and were cultured in an incubator at 37° C. and 5% $CO_2$ for 24 hours. Vero E6 cells were seeded at $5\times10^5$ cells per well into respective wells of 6-well plates containing serum-free MEM, and were cultured in an incubator at 33° C. and 5% $CO_2$ for 24 hours. Thereafter, the cells were infected with the abovementioned virus diluent solution, and the viruses were allowed to adsorb at 37° C. (33° C. for HCoV-OC43-infected Vero-E6 cells) for 1 hour.

Afterwards, the infected cells were washed with PBS, and then 3 mL of an agarose overlay medium (0.3% agarose in DMEM or MEM containing 2% FBS) was added to each well. After the agarose overlay medium had solidified, the plates were placed in an incubator set at 37° C. or 33° C.

After incubation for a given time period, the cells in each well were fixed with 2 mL of a 10% formaldehyde solution at room temperature for 2 hours. Next, the solidified agarose overlay in each well was removed, and then the fixed cells in each well were stained with 0.5% crystal violet (Manufacturer: Sigma Aldrich) for 2 min. After rinsing the stained cells with water, the viral plaques in each well were counted. The viral titer (plaque forming units (P.F.U.)/mL) was determined by the following formula (1):

$$A=B/(C\times 0.5) \qquad (1)$$

wherein: A=viral titer
B=the viral plaques counted
C=the dilution factor of the virus 4. Quantitative Viral RNA Expression Total RNA was extracted using TRIzol™ Reagent (Invitrogen), and 1 µg RNA was used as a template for synthesizing cDNA by reverse transcription polymerase chain reaction (RT-PCR) using ReverTraAce™ qPCR RT kit (Toyobo). Thereafter, the thus obtained cDNA, serving as a DNA template, was subjected to quantitative real-time PCR (qRT-PCR), which was performed on a LightCycler®480 System (Roche Life Science) using a designed primer pair specific for enterovirus 5' untranslated region (UTR) and the reaction conditions shown in Table 1, so as to determine the viral RNA expression level. An actin expression level determined using an actin-specific primer pair under the same reaction conditions was used as an internal control.

TABLE 1

| Contents | | Volume (µL) | |
|---|---|---|---|
| cDNA | | 1 | |
| Enterovirus 5' UTR-specific primer pair | Forward primer (10 µM): 5'-ccctgaatgcggctaatc-3' (SEQ ID No: 1) | 0.2 | 0 |
| | Reverse primer (10 µM): 5'-attgtcaccataagcagcca-3' (SEQ ID No: 2) | 0.2 | 0 |
| Actin-specific primer pair (internal control) | Forward primer (10 µM): 5'-gctcgtcgtcgacaacggctc-3' (SEQ ID No: 3) | 0 | 0.2 |
| | Reverse primer (10 µM): 5'-caaacatgatcctgggtcatcttctc-3' (SEQ ID No: 4) | 0 | 0.2 |
| KAPA SYBR FAST qPCR Master Mix (2X) (KAPABiosystems) | | 5 | |
| DEPC-treated d₂H₂O | | 3.6 | |

Operation conditions: Denaturation at 95° C. for 3 min, followed by 45 cycles of the following reactions: denaturation at 95° C. for 5 sec, and primer annealing and extension at 60° C. for 20 sec.

5. Statistical Analysis

The experimental data are expressed as mean±standard error of the mean (SEM) of independent experiments performed in triplicates, and were analyzed by Student's two-tailed unpaired t-test using GraphPad Prism 6 software (GraphPad Software, Inc., California, USA), where p-values<0.05 were considered to be statistically significant.

Example 1. Identification of Common Host Factors Involved in Virus Replication Using Genome-Wide CRISPR-Cas9 Knockout Screens A549 cells were transduced with a pool of lentiviruses each containing a puromycin resistance gene and a specific single-guide RNA (sgRNA) from the GeCKO v2 human library (obtained from Taiwan National RNAi Core Facility, Academia Sinica) at a m.o.i. of <0.3 for two days. Then, the transduced cells were subjected to puromycin selection for 7 days to achieve maximal knockout efficiency so as to generate a library of sgRNA-expressing cells. Thereafter, these sgRNA-expressing cells were infected with CV-A6 at m.o.i. of 1. Genomic DNA was harvested from the surviving infected cells and uninfected cells (i.e., mock infection) at designated time points post-infection. Subsequently, sgRNA regions were amplified from the genomic DNA and then subjected to deep sequencing using NextSeq platform (Illumina), followed by analysis using Model-based Analysis of Genome-wide CRISPR/Cas9 Knockout (MAGeCK) v0.56 (Li et al. (2014), *Genome Biol.*, 15:554) to identify candidate genes that may be crucial to virus replication.

There are 20 top candidate genes enriched by CV-A6 challenge which may be involved in enterovirus replication include ACSL4 (Acyl-CoA synthetase long-chain family member 4), LPCAT3, ZBTB21, DPY30, DHX36, C11orf31, ZFPM1, PALM2, SNAP47, SPTLC2, RPL36A, FAM21A, TUSC5, LFNG, LRRC42, MYOZ2, HMBS, PPP1R14D, MS4A1, and CHODL (data not shown). In the following experiments, the applicants selected ACSL4 for further analysis and then established ACSL4 knockdown and ACSL4 knockout stable cells so as to investigate the biological roles of ACSL4 in virus replication.

Example 2. Evaluation of the Effect of ACSL4 on Enterovirus Replication

A. Establishment of ACSL4 Knockdown and Knockout Cells (i) ACSL4 Knockdown Stable Cells Two short hairpin RNAs (shRNAs) (i.e., TRCN0000045539 and TRCN0000045541) targeting human ACSL4 mRNA at nucleotide positions 485 to 505 (shACSL4#39, 5-ccagtgttgaacttctggaaa-3', SEQ ID No: 5) and nucleotide positions 439 to 459 (shACSL4#41, 5-gcagtagttcatgggctaaat-3', SEQ ID No: 6), respectively, and a scramble control shRNA (shNC, 5'-aatttgcgcccgct-tacccagtt-3', SEQ ID No: 7), were each inserted into lentivirus vectors pLKO_TRC005 (obtained from Taiwan National RNAi Core Facility, Academia *Sinica*) according to the instructions of the Taiwan National RNAi Core Facility, Academia *Sinica*, so as to construct three pLKO-shRNA vectors, i.e., pLKO.1-shACSL4#39, pLKO.1-shACSL4#41 and pLKO_TRC005-shNC.

For lentivirus preparation, 293T cells were co-transfected with pLKO.1-shACSL4#39, pLKO.1-shACSL4#41 or pLKO_TRC005-shNC, in combination with the helper plasmids pMD.G and pCMVAR8.91, using X-tremeGENE transfection reagent (Roche), and then cultured at 37° C. for 36 hours. After centrifugation under 300×g, the resultant supernatant containing viral particles was harvested.

The RD or A549 cells were transduced with the obtained viral particles for 24 hours, and then subjected to selection with puromycin (5 µg/mL), so as to prepare RD-shACSL4#39, RD-shACSL4#41, and A549-shACSL4#39 stable cells with sustained knockdown of endogeneous ACSL4 gene expression, and RD-shNC and A549-shNC control cells.

(ii) ACSL4 Knockout Stable Cells

A single guide RNA (sgRNA) targeting human ACSL4 mRNA at nucleotide positions 386 to 405 (sgACSL4$^{-/-}$, 5'-aggaaagttgtacttaaagc-3', SEQ ID No: 8) was inserted into a lentivirus vector lentiCRISPRv2 (obtained from Dr. Feng Zhang, Broad Institute of MIT and Harvard, Cambridge, Mass., USA) that contains the humanized SpCas9 enzyme, so as to construct lentiCRISPRv2-sgACSL4$^{-/-}$ vector. After that, 293T cells were co-transfected with lentiCRISPRv2-sgACSL4$^{-/-}$, and the packaging plasmids pMD.G and pCM- VAR8.91, using X-tremeGENE transfection reagent (Roche). The viral particles were harvested from supernatant of the cell culture. Subsequently, RD cells were transduced with the obtained viral particles for 24 hours, and then subjected to selection with puromycin (2 μg/mL), so as to prepare RD-sgACSL4$^{-/-}$ stable cells with ACSL4 gene knockout. RD-sgACSL4$^{+/+}$ stable cells (mock infection) with normal ACSL4 gene expression were also prepared for serving as a control group.

(iii) Determination of ACSL4 Protein Expression in ACSL4 Knockdown and Knockout Stable Cells Each of the RD-shACSL4#39, RD-shACSL4#41, RD-shNC, RD-sgACSL4$^{-/-}$ and RD-sgACSL4$^{+/+}$ cells were seeded in a 12-well plate at a concentration of $2\times10^5$ cells per well. After 24 hours, the cells were washed with PBS and lysed with IGEPAL CA630 lysis buffer (150 mM NaCl, 1% IGEPAL CA630, 50 mM Tris-base [pH 8.0]) for 30 minutes on ice. The resultant cell lysates were centrifuged at $10,000\times g$ for 10 minutes at 4° C., and the supernatants were collected to serve as total protein samples. Total protein samples in equal amount (determined by Bradford assay) were subjected to immunoblot analysis according to the procedures as described in the preceding section, entitled "2. Western blot analysis," of the General Experimental Procedures. Actin was used as a loading control. The primary and secondary antibodies used for detecting the respective protein in this example are shown in Table 2 below.

TABLE 2

| Proteins | Primary antibody | Secondary antibody |
| --- | --- | --- |
| ACSL4 (A-5) | Mouse monoclonal anti-ACSL4 antibody (Cat. No. sc-271800, Santa Cruz Biotechnology, CA) | Amersham ECL Mouse IgG, HRP-linked whole antibody (from sheep) (Cat. No. NA931, GE Healthcare) |
| Actin | Mouse monoclonal anti-actin antibody (Cat. No. MAB1501 Millipore, MA) | Amersham ECL Mouse IgG, HRP-linked whole antibody (from sheep) |

Figure 1:
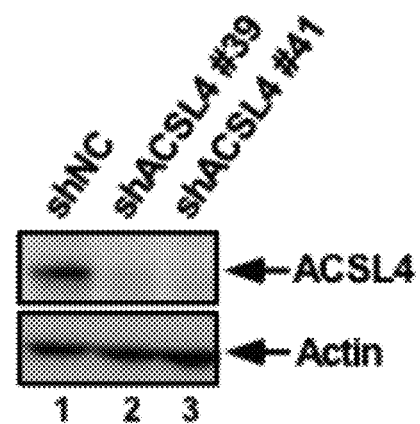
FIG. 1 shows protein expression of Acyl-CoA synthetase long chain family member 4 (ACSL4) in ACSL4 knockdown stable cells (i.e., shACSL4#39 and shACSL4#41 cells) and shNC control cells (upper panel) and in ACSL4 knockout stable cells (i.e., sgACSL4$^{-/-}$ cells) and sgACSL4$^{+/+}$ control cells (lower panel), in which actin served as a loading control.
Figure 1:
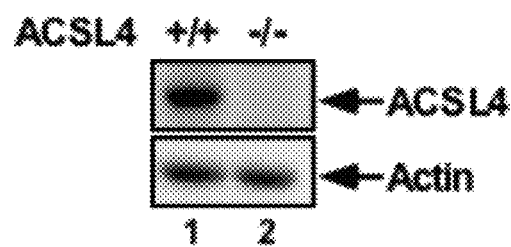

FIG. 1 illustrates Western blot results of ACSL4 expression in ACSL4 knockdown cells (upper panel), and in ACSL4 knockout cells (lower panel). As shown in the upper panel of FIG. 1, the expression of ACSL4 was dramatically reduced in RD-shACSL4#39 and RD-shACSL4#41 knockdown stable cells (as compared to the RD-shNC control cells). The similar phenomenon is recapitulated in the lower panel of FIG. 1, in which RD-sgACSL4$^{-/-}$ knockout stable cells show no ACSL4 expression (as compared to the RD-sgACSL4$^{+/+}$ control cells). These results verify the absence or substantial absence of ACSL4 protein expression in these ACSL4 knockdown and ACSL4 knockout cells.

B. Determining the Viral Titer and Viral RNA Expression in Enterovirus-Infected ACSL4 Knockdown/Knockout Cells (i) Determination of Viral Titer According to the procedures as described in the preceding sections, entitled "1. Viral infection," and "3. Viral plaque assay," of the General Experimental Procedures, the RD-shACSL4#39, RD-shACSL4#41, RD-shNC, RD-sgACSL4$^{-/-}$ and RD-sgACSL4$^{+/+}$ cells as prepared in the above A section were infected with CV-A6 at m.o.i. of 0.01, and then the CV-A6 viruses in the infected RD-shACSL4#39, RD-shACSL4#41, RD-shNC, RD-sgACSL4$^{-/-}$ and RD-sgACSL4$^{+/+}$ cells were harvested at 12, 24, and 36 hours post-infection (h.p.i.) for determination of virus titer.

FIG. 2 shows virus titers (expressed as log P.F.U./mL) of the CV-A6 respectively in the infected ACSL4 knockdown cells (upper panel) and the infected ACSL4 knockout cells (lower panel) at 12, 24, and 36 h.p.i. As shown in FIG. 2, compared to the RD-shNC control cells, the viral titers of CV-A6 significantly decreased by 81%, 92% and 74% at 12, 24, and 36 h.p.i., respectively in RD-shACSL4#39 knockdown cells, and decreased by 97%, 80% and 50% at 12, 24, and 36 h.p.i., respectively in the RD-shACSL4#41 knockdown cells. In addition, the viral titer of CV-A6 significantly decreased by 95%, 76% and 55% at 12, 24, and 36 hours h.p.i. respectively, in the RD-sgACSL4$^{-/-}$ knockout cells compared to that in the RD-sgACSL4$^{+/+}$ control cells.

To further determine whether ACSL4 is also involved in the replication of other enterovirus species/serotypes, the RD-sgACSL4$^{-/-}$ and RD-sgACSL4$^{+/+}$ cells were infected with a respective one of EV-A71 at m.o.i. of 0.001, EV-D68 at m.o.i. of 0.001, CV-A16 at m.o.i. of 0.1, and CV-B3 at m.o.i. of 0.001. Then, for determination of virus titer, the EV-A71 and EV-D68 in the infected cells were harvested at 24 and 36 h.p.i., the CV-A16 in the infected cells were harvested at 24 and 48 h.p.i., and the CV-B3 in the infected cells were harvested at 12 and 24 h.p.i.

FIG. 3 shows virus titers (expressed as P.F.U./mL) of each of EV-A71, EV-D68, CV-A16, and CV-B3 in the infected ACSL4 knockout cells at the indicated h.p.i. As shown in FIG. 4, compared to the RD-sgACSL4$^{+/+}$ control cells, the viral titers of EV-A71, EV-D68, CV-A16, and CV-B3 show significant decrease in the infected RD-sgACSL4$^{-/-}$ knockout cells.

(ii) Determination of Viral RNA Expression

According to the procedures as described in the preceding section, entitled "1. Virus infection," of the General Experimental Procedures, the RD-shACSL4#39, RD-shACSL4#41, RD-shNC, RD-sgACSL4$^{-/-}$ and RD-sgACSL4$^{+/+}$ cells were infected with CV-A6 at m.o.i. of 0.01. In addition, the RD-sgACSL4$^{-/-}$ and RD-sgACSL4$^{+/+}$ cells were also infected with a respective one of EV-A71 at m.o.i. of 0.001, EV-D68 at m.o.i. of 0.001, CV-A16 at m.o.i. of 0.1, and CV-B3 at m.o.i. of 0.001.

The CV-A6-infected cells were harvested at 12, 24 and 36 hours h.p.i., the EV-A71-infected cells and EV-D68-infected cells were harvested at 24 and 36 h.p.i., the CV-A16-infected cells were harvested at 24 and 48 h.p.i., and the CV-B3-infected cells were harvested at 12 and 24 h.p.i. Then, the infected cell thus harvested were subjected to determination of viral RNA expression level according to the procedures as described in the preceding section, entitled "4. Quantitative viral RNA expression," of the General Experimental Procedures. The relative viral RNA level (normalized by actin RNA expression level) in the infected RD-shNC control cells and the infected RD-sgACSL4$^{+/+}$ control cells was set as 100%.

FIG. 4 shows relative viral RNA level in the CV-A6-infected ACSL4 knockdown cells (upper panel), and in the CV-A6-infected ACSL4 knockout cells (lower panel), at 12, 24, and 36 h.p.i. As shown in FIG. 4, compared to the CV-A6-infected RD-shNC control cells, the relative viral RNA level in the CV-A6-infected RD-shACSL4#39 and RD-shACSL4#41 knockdown cells significantly decreased at 12, 24, and 36 h.p.i. In addition, compared to the CV-A6-infected RD-sgACSL4$^{+/+}$ control cells, the relative viral RNA levels also significantly decreased in the CV-A6-infected RD-sgACSL4$^{-/-}$ knockout cells at 12, 24, and 36 h.p.i.

FIG. 5 shows relative viral RNA level in the ACSL4 knockout cells infected by different enteroviruses. As shown in FIG. 5, compared to enterovirus-infected RD-sgACSL4$^{+/+}$ control cells, the relative viral RNA level in the RD-sgACSL4$^{-/-}$ knockout cells infected by a respective one of EV-A71, EV-D68, CV-A16, and CV-B3 significantly decreased at the specified h.p.i.

Taken together, these results indicate that ACSL4 is the common host factor critical for the replication of enteroviruses, such as CV-6, EV-A71, EV-D68, CV-A16 and CV-B3.

Example 3. Evaluation of the Effect of ACSL4 on Replication of Other RNA Viruses In this example, the ACSL4 knockdown cells was infected with other RNA viruses including coronavirus (such as HCoV-229E), influenza virus (such as IAV) and flavivirus (such as ZIKV), so as to determine the effect of ACSL4 on RNA virus replication.

A. Determining Viral Protein Expression in IAV-Infected and ZIKV-Infected ACSL4 Knockdown Cells The A549-shACSL4#39 and A549-shNC cells were infected with IAV at m.o.i. of 0.001, and the A549-shACSL4#39 and A549-shNC cells were infected with ZIKV at m.o.i. of 0.1 according to the procedures as described in the preceding section, entitled "1. Virus infection," of the General Experimental Procedures. At 24, 48, and 72 h.p.i., the IAV-infected cells and the ZIKV-infected cells were washed with PBS and lysed with IGEPAL CA630 lysis buffer (150 mM NaCl, 1% IGEPAL CA630, 50 mM Tris-base [pH 8.0]) for 30 minutes on ice. Each of the resultant cell lysates was centrifuged at 10,000×g for 10 minutes at 4° C., and the resultant supernatants were respectively collected to serve as a total protein sample for a respective one of the infected cells. Total protein samples in equal amount (determined by Bradford assay) were subjected to immunoblot analysis according to the procedures as described in the preceding section, entitled "2. Western blot analysis," of the General Experimental Procedures. Actin and glyceraldehyde-3-phosphate dehydrogenase (GAPDH) were used as a loading control for IAV-infected cells and ZIKV-infected cells, respectively. The primary and secondary antibodies used for detecting viral proteins i.e., IAV M1 protein, and ZIKV NS2B and NS3 proteins) and host cell proteins (i.e., ACSL4 protein, actin and GAPDH) in this example are shown in Table 3 below.

TABLE 3

| Proteins | Primary antibody | Secondary antibody |
|---|---|---|
| IAV M1 | Rabbit polyclonal anti-influenza A virus M1 (matrix protein) antibody (Cat. No. GTX125928, GeneTex) | Amersham ECL Mouse IgG, HRP-linked whole antibody (from sheep) (Cat. No. NA931, GE Healthcare) |
| ZIKV NS2B | Rabbit polyclonal anti-Zika virus NS2B antibody (Cat. No. GTX133308, GeneTex) | Amersham ECL Mouse IgG, HRP-linked whole antibody (from sheep) |
| ZIKV NS3 | Rabbit polyclonal anti-Zika virus NS3 antibody (Cat. No. GTX133309, GeneTex) | Amersham ECL Mouse IgG, HRP-linked whole antibody (from sheep) |
| ACSL4 (A-5) | Mouse monoclonal anti-ACSL4 antibody (Cat. No. sc-271800, Santa Cruz Biotechnology) | Amersham ECL Mouse IgG, HRP-linked whole antibody (from sheep) |
| Actin | Mouse monoclonal anti-actin antibody (Cat. No. MAB1501 Millipore) | Amersham ECL Mouse IgG, HRP-linked whole antibody (from sheep) |
| GAPDH | Mouse monoclonal anti-actin antibody (Cat. No. H00002597-M01 Abnova) | Amersham ECL Mouse IgG, HRP-linked whole antibody (from sheep) |

FIG. 6 illustrates Western blot results of viral proteins in IAV-infected A549-shACSL4#39 knockdown cells (upper panel), and in ZIKV-infected A549-ACSL4#39 knockdown cells (lower panel) at 24, 48, and 72 h.p.i. As shown in FIG. 6, IAV M1 protein expression was gradually reduced and ACSL4 protein expression was significantly reduced in IAV-infected A549-shACSL4#39 knockdown cells as compared to the IAV-infected A549-shNC control cells at 24, 48, and 72 h.p.i, and the same phenomenon is recapitulated in ZIKV-infected A549-shACSL4#39 knockdown cells as compared to the ZIKV-infected A549-shNC control cells, indicating the viral protein expression can be reduced in these ACSL4 knockdown cells. Therefore, it is inferred that virus replication in the infected cells may be reduced by targeting ACSL4.

B. Determining the Viral Titer in IAV-Infected and ZIKV-Infected ACSL4 Knockdown Cells According to the procedures as described in the preceding section, entitled "1. Viral infection," of the General Experimental Procedures, the A549-shACSL4#39 and A549-shNC cells were infected with IAV at m.o.i. of 0.001, and the A549-shACSL4#39 and A549-shNC cells were infected with ZIKV at m.o.i. of 0.1. Then, the viruses in the infected cells were harvested at 24, 48, and 72 h.p.i. for determination of virus titer according to the procedures as described in the preceding section, entitled "3. Viral plaque assay," of the General Experimental Procedures, in which MDCK and Vero cells were used to determine virus titers of IAV and ZIKA, respectively.

FIG. 7 shows virus titers (expressed as log P.F.U./mL) of the IAV in the infected ACSL4 knockdown cells (upper panel), and of the ZIKV in the infected ACSL4 knockdown cells (lower panel) at 24, 48, and 72 h.p.i. As shown in FIG. 7, compared to the control cells, the viral titer of each of IAV and ZIKV decreased at 24, 48, and 72 h.p.i. in ACSL4 knockdown cells.

C. Determining the Viral Titer in HCoV-229E-Infected ACSL4 Knockout Cells

According to the procedures as described in the preceding section, entitled "1. Viral infection," of the General Experimental Procedures, the RD-sgACSL4$^{-/-}$ and RD-sgACSL4$^{+/+}$ cells were infected with HCoV-229E at m.o.i. of 0.01. Then, the viruses in the infected cells were harvested at 1, 2, 3, and 4 days post-infection (d.p.i.) for determination of virus titer according to the procedures as described in the preceding section, entitled "3. Viral plaque assay," of the General Experimental Procedures, in which Huh-7 cells were used to determine virus titer of HCoV-229E.

FIG. 8 shows virus titer (expressed as P.F.U./mL) of HCoV-229E in the infected ACSL4 knockout cells at the indicated d.p.i. As shown in FIG. 8, the viral titer of HCoV-229E show significant decrease in the infected RD-sgACSL4$^{-/-}$ knockout cells compared to the RD-sgACSL4$^{+/+}$ control cells.

Collectively, these results indicate that ACSL4 is a common host factor involved in the replication of single-strand RNA viruses including HCoV-229E, IAV and ZIKV.

Example 4. Determining the Role of ACSL4 in Virus-Infected Cells

Previous studies have demonstrated that ACSL4 plays a vital role in ferroptosis (Doll et al. (2017), Nat. Chem. Biol., 13:91-98; Yuan et al. (2016), Biochem. Biophys. Res. Commun., 478:1338-1343), an iron-dependent, non-apoptotic regulatory cell death (Dixon et al. (2012), Cell, 149:1060-

1072) that is characterized by accumulation of lethal lipid peroxides, especially phosphatidylethanolamine-OOH (PE-OOH), and ACSL4 is identified as the key enzyme involved in the formation of oxidized arachidonoyl (AA)-containing PE or adrenoyl (AdA)-containing PE, accumulation of which can induce ferroptosis (Kagan et al. (2017), Nat. Chem. Biol., 13:81-90). In order to determine whether virus infection induces ferroptosis through ACSL4, the following experiments were conducted.

A. Determining Lipid Peroxidation Level in Virus-Infected Cells

Since lipid peroxidation is the hallmark of ferroptosis, BODIPY™ 581/591-C11 (Invitrogen), which is an oxidation-sensitive fluorescent lipid peroxidation probe, was employed to detect lipid peroxidation in virus-infected cells.

Specifically, the RD-sgACSL4$^{-/-}$ knockout and RD-sgACSL4$^{+/+}$ control cells were seeded in 12-well plates at a concentration of $1 \times 10^5$ cells per well. After 24 hours, the cells were treated with 1 μM of RSL3 (RAS-selective lethal) (Sigma), which is an inducer of ferroptosis and which serves as positive control for lipid peroxidation, for 36 hours, or with the same concentration of DMSO serving as control group for comparison purpose.

In a parallel experiment, the RD-sgACSL4$^{-/-}$ knockout and RD-sgACSL4$^{+/+}$ control cells seeded as mentioned above were infected with CV-A6 at m.o.i. of 0.01 for 36 hours according to the procedures as described in the preceding section, entitled "1. Virus infection," of the General Experimental Procedures, and mock-infected cells served as control groups.

Next, the treated cells and the infected cells were stained by incubating with 1 μM BODIPY™ 581/591-C11 (Invitrogen) at 37° C. for 30 minutes, and then collected using trypsin (Gibco). Thereafter, the stained cells were subjected to centrifugation at 300 g for 10 minutes to remove trypsin and the cell culture media, and then resuspended in 500 μL of fresh PBS. Subsequently, at least 10000 cells per sample were subjected to flow cytometry analysis using Attune NxT flow cytometer (Invitrogen), and FlowJo software was used for viewing and analyzing the thus obtained data. The BODIPY™ 581/591-C11 levels in the control groups (i.e., DMSO-treated cells and mock-infected cells) were set as 100%.

FIG. 9 shows relative level of BODIPY™ 581/591-C11 (i.e., indicator for lipid peroxidation level) in the RSL3-treated ACSL4 knockout cells (upper panel), and in the CV-A6-infected ACSL4 knockout cells (lower panel). As shown in FIG. 9, RSL3 is capable of effectively induce lipid peroxidation in the cells with normal ACSL4 expression, but is unable to induce lipid peroxidation in ACSL4 knockout cells. In addition, lipid peroxidation increased about 4.5-fold in the CV-A6-infected cells with normal ACSL4 expression as compared to mock-infected cells. However, when compared with mock-infected ACSL4 knockdown cells, only a mere 1.5-fold increase in lipid peroxidation is shown in the CV-A6-infected ACSL4 knockdown cells. In particular, for the CV-A6-infected cells, lipid peroxidation is significantly reduced in the ACSL4 knockdown cells as compared to the cells with normal ACSL4 expression.

To further determine whether coronavirus also induces ferroptosis, LLC-MK2 cells were seeded in 12-well plates at a concentration of $1 \times 10^5$ cells per well. After 24 hours, the cells were infected with HCoV-229E at m.o.i. of 0.01 according to the procedures as described in the preceding section, entitled "1. Virus infection," of the General Experimental Procedures, and mock-infected cells served as control group. At 2, 3, 4, and 5 d.p.i., the cells were subjected to staining with BODIPY™ 581/591-C11 followed by flow cytometry analysis according to the experimental procedures as described above. The BODIPY™ 581/591-C11 level in the control group (i.e., mock-infected cells) were set as 100%.

FIG. 10 shows relative level of BODIPY™ 581/591-C11 (i.e., indicator for lipid peroxidation level) in the HCoV-229E-infected LLC-MK2 cells at 2, 3, 4, and 5 d.p.i. As shown in FIG. 10, lipid peroxidation is effectively induced in the HCoV-229E-infected LLC-MK2 cells as compared to mock-infected cells.

These results suggest that virus infection can induce ferroptosis through ACSL4. Therefore, it is inferred that, a ferroptosis inhibitor (such as ACSL4 inhibitor) may be useful to inhibit viral replication. To demonstrate such inference, the following experiments are conducted using two known ferroptosis inhibitors including ferrostatin-1 and troglitazone.

B. Determining the Effect of Ferroptosis Inhibitors on Lipid Peroxidation Level of Virus-Infected Cells Wild-type RD cells were seeded in 12-well plates at a concentration of $1 \times 10^5$ cells per well. After 24 hours, the cells were pretreated with a respective one of ferrostatin-1 and troglitazone, at concentrations of 100 μM and 20 μM, respectively, for 1 hour. Subsequently, the pretreated cells were treated with 1 μM of RSL3 for 36 hours, or the same amount of DMSO serving as control group for comparison purpose.

In a parallel experiment, the pretreated cells were infected with CV-A6 at m.o.i. of 0.01 for 36 hours according to the procedures as described in the preceding section, entitled "1. Virus infection," of the General Experimental Procedures, and mock-infected cells served as control group. Thereafter, these cells were subjected to staining with BODIPY™ 581/591-C11 (Invitrogen) and flow cytometry analysis according to the experimental procedures as described in the preceding sub-section, entitled "A. Determining lipid peroxidation level in virus-infected cells," of this Example. The BODIPY™ 581/591-C11 levels in the control groups (i.e., DMSO-treated cells and mock-infected cells) were set as 100%.

FIG. 11 shows relative level of BODIPY™ 581/591-C11 (i.e., indicator for lipid peroxidation level) in the RSL3-treated cells pretreated with a respective one of ferrostatin-1 and troglitazone (upper panel), and in the CV-A6-infected cells pretreated with a respective one of ferrostatin-1 and troglitazone (lower panel). As shown in FIG. 11, there was a significant increase in lipid peroxidation levels in RSL3-treated cells and CV-A6-infected cells, as respectively compared with DMSO-treated cells and mock-infected cells, and such increase was significantly diminished in the cells pretreated with a respective one of ferrostatin-1 and troglitazone.

Taken together, these results indicate that ferroptosis inhibitors can effectively reduce viral infection-induced ferroptosis, and thus are capable of inhibiting virus infection and replication.

Example 5. Evaluation of the Effect of Ferroptosis Inhibitors on Cell Viability and Viral Titer in Virus-Infected Cells To further evaluate whether ferroptosis inhibitors including ferrostatin-1 and troglitazone can reduce virus replication in infected host cells, the following experiments were conducted.

A. Determining Cell Viability of Virus-Infected Cells

Wild-type RD cells and LLC-MK2 cells were seeded at a concentration of 2000 cells per well into respective wells of 96-well plates containing DMEM and 10% FBS. After culturing for 24 hours, the cells were pretreated with a respective one of ferrostatin-1 and troglitazone, at concentrations of 0, 5, 10, 20, 40, 60, 80, 100, and 120 μM, respectively, for 1 hour. Subsequently, according to the procedures as described in the preceding section, entitled "1. Virus infection," of the General Experimental Procedures, the ferrostation-1-pretreated and troglitazone-pretreated RD cells were infected with CV-A6 at m.o.i. of 0.01 for 36 hours, and the ferrostation-1-pretreated and troglitazone-pretreated LLC-MK2 cells were infected with HCoV-229E at m.o.i. of 0.01 for 7 days. Mock-infected RD and LLC-MK2 cells served as control groups. CV-A6-infected and mock-infected RD cells, and HCoV-229E-infected and mock-infected LLC-MK2 cells were subjected to cell viability determination using CellTiter96 Aqueous One Solution Cell Proliferation Assay (Promega).

Results:

FIGS. 12 and 13 respectively shows cell viability of CV-A6-infected and mock-infected RD cells that were pretreated with increasing concentrations of ferrostatin-1 and troglitazone, and cell viability of HCoV-229E-infected and mock-infected LLC-MK2 cells that were pretreated with increasing concentrations of ferrostatin-1 and troglitazone.

As shown in FIGS. 12 and 13, ferrostatin-1 and troglitazone are capable of increasing cell viability of CV-A6-infected cells and HCoV-229E-infected LLC-MK2 cells as compared to their control groups, indicating that infection of RNA viruses, such as enterovirus (e.g., CV-A6) and coronavirus (e.g., HCoV-229E), can be inhibited by the ferroptosis inhibitors.

B. Determining Viral Titer in Virus-Infected Cells

Wild-type RD cells were seeded at a concentration of $2\times10^5$ cells per well into respective wells of 12-well plates containing serum-free DMEM. LLC-MK2 cells and Vero E6 cells were seeded at a concentration of $2\times10^5$ cells per well into respective wells of 12-well plates containing serum-free MEM.

After culturing for 24 hours, the RD cells were pretreated with a respective one of ferrostatin-1 and troglitazone at concentrations of 100 μM and 20 μM for 1 hour. The LLC-MK2 cells were pretreated with a respective one of ferrostatin-1 (40 μM) and troglitazone (10 μM) for 1 hour. The Vero E6 cells were pretreated with a respective one of ferrostatin-1 (40 μM) and troglitazone (10 μM) for 1 hour.

The pretreated RD cells were infected with CV-A6 at m.o.i. of 0.01, the pretreated LLC-MK2 cells were infected with HCoV-229E at m.o.i. of 0.01, and the pretreated Vero E6 cells were infected with HCoV-OC43 at m.o.i. of 0.01. The CV-A6 in the infected RD cells were harvested at 24, 36, and 48 h.p.i., and the HCoV-229E in the infected LLC-MK2 cells and the HCoV-OC43 in the infected Vero E6 cells were harvested at 1, 2, and 3 d.p.i. for determination of virus titer according to the procedures as described in the preceding section, entitled "3. Viral plaque assay," of the General Experimental Procedures.

In comparison, wild-type RD cells, LLC-MK2 cells and Vero E6 cells pretreated with dimethyl sulfoxide (DMSO) (serving as control groups) were subjected to the same analysis.

Results:

FIG. 14 shows virus titers (expressed as log P.F.U./mL) of the CV-A6 in the infected RD cells respectively pretreated with ferrostatin-1 and troglitazone. As shown in FIG. 14, as compared to the control group, viral yields of the CV-A6 in the infected RD cells pretreated with a respective one of ferrostatin-1 and troglitazone are significantly lower, indicating that ferrostatin-1 and troglitazone are effective in reducing viral replication in host cells infected with enterovirus.

FIG. 15 shows virus titers (expressed as log P.F.U./mL) of the HCoV-229E and HCoV-OC43 respectively in the infected LLC-MK2 cells pretreated with ferrostatin-1 or troglitazone and in the infected Vero E6 cells pretreated with ferrostatin-1 or troglitazone. As shown in FIG. 15, as compared to the control groups, viral yields of the HCoV-229E and HCoV-OC43 in the infected cells pretreated with a respective one of ferrostatin-1 and troglitazone are significantly lower, indicating that ferrostatin-1 and troglitazone are effective in reducing viral replication in host cells infected with coronavirus.

Taken together, these results demonstrate that ferroptosis inhibitors such as ferrostatin-1 and troglitazone, can effectively inhibit virus infection and replication by downregulating ACSL4 expression in the infected cells to exert an anti-ferroptosis effect.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for inhibiting virus infection, comprising administering to a subject in need thereof an effective amount of a ferroptosis inhibitor or a pharmaceutically acceptable salt thereof,
   wherein the ferroptosis inhibitor is selected from the group consisting of ferrostatin-1, troglitazone, rosiglitazone, pioglitazone, triacsin C, liproxstatin-1, and combinations thereof, and
   wherein the virus infection is caused by an enterovirus selected from the group consisting of Coxsackie virus A6 (CV-A6), Coxsackie virus A16 (CV-A16), Enterovirus A71 (EV-A71), Coxsackie virus B3 (CV-B3), Enterovirus D68 (EV-D68), and combinations thereof.

2. The method as claimed in claim 1, wherein the ferroptosis inhibitor or the pharmaceutically acceptable salt thereof is in a dosage form for oral administration.

3. A method for inhibiting viral replication, comprising contacting a virus with a ferroptosis inhibitor or a pharmaceutically acceptable salt thereof,
   wherein the ferroptosis inhibitor is selected from the group consisting of ferrostatin-1, troglitazone, rosiglitazone, pioglitazone, triacsin C, liproxstatin-1, and combinations thereof, and
   wherein the virus is an enterovirus selected from the group consisting of Coxsackie virus A6 (CV-A6), Coxsackie virus A16 (CV-A16), Enterovirus A71 (EV-A71), Coxsackie virus B3 (CV-B 3), Enterovirus D68 (EV-D68), and combinations thereof.

* * * * *